US012668765B2

(12) United States Patent
Cho et al.

(10) Patent No.: US 12,668,765 B2
(45) Date of Patent: Jun. 30, 2026

(54) MICROFLUIDIC SYSTEM SIMULATING LUNG TISSUE

(71) Applicant: Seoul National University Hospital, Seoul (KR)

(72) Inventors: Young-Jae Cho, Seongnam-Si (KR); Mi-Young Park, Seongnam-Si (KR); Eun Young Eo, Seongnam-Si (KR)

(73) Assignee: Seoul National University Hospital, Seoul (KR)

( * ) Notice: Subject to any disclaimer, the term of this patent is extended or adjusted under 35 U.S.C. 154(b) by 1128 days.

(21) Appl. No.: 17/764,168

(22) PCT Filed: Sep. 29, 2020

(86) PCT No.: PCT/KR2020/013365
§ 371 (c)(1),
(2) Date: Sep. 15, 2022

(87) PCT Pub. No.: WO2021/066537
PCT Pub. Date: Apr. 8, 2021

(65) Prior Publication Data
US 2023/0002714 A1      Jan. 5, 2023

(30) Foreign Application Priority Data

Sep. 30, 2019      (KR) ........................ 10-2019-0120834

(51) Int. Cl.
*C12M 3/06*          (2006.01)
*C12M 1/00*          (2006.01)
(Continued)

(52) U.S. Cl.
CPC ............ *C12M 23/16* (2013.01); *C12M 21/08* (2013.01); *C12M 23/22* (2013.01); *C12M 25/16* (2013.01);
(Continued)

(58) Field of Classification Search
CPC .............................. C12M 23/16; C12M 21/08
See application file for complete search history.

(56) References Cited

U.S. PATENT DOCUMENTS

2014/0308688 A1    10/2014   Grego et al.
2014/0335496 A1    11/2014   Grego et al.
(Continued)

FOREIGN PATENT DOCUMENTS

CN            102124096 A      7/2011
CN            104830683 A      8/2015
(Continued)

OTHER PUBLICATIONS

Li Kaiyan et al., "Biomimetic human lung-on-a-chip for modeling disease investigation," Biomicrofluidics, vol. 13, No. 3, (May 2019).
(Continued)

*Primary Examiner* — Jonathan M Hurst
(74) *Attorney, Agent, or Firm* — Jackson Walker LLP

(57)                    ABSTRACT

Disclosed are a biomimic system simulating lung tissue, a method for manufacturing same, and a microfluidic control method using same, wherein the biomimic system comprises lung epithelial cells and lung fibroblasts, which are isolated from human lungs, and commercially available vascular endothelial cells, and wherein a microfluid flows through the biomimic system. Each chamber inside the corresponding system can allow a fluid, which contains gas and a medium, to flow therethrough and simulate respiration-like movement, wherein all of the three types of cells can survive inside the system even when one week or more have elapsed after through-flow of the fluid. In addition, the pH and $pO_2$ in the chamber can be monitored by using a pH sensor and a gas partial pressure sensor inside the system, and thus the three types of cells inside the system can be exposed to external environments, drugs, and the like under the same (Continued)

conditions as in the lungs in vivo. Therefore, a wide range of studies including modeling of lung diseases by harmful substances and testing of therapeutic drug efficacy can be conducted, and further, the utilization to in vitro disease modeling, customized medicine prescriptions, and the like can also be made.

3 Claims, 30 Drawing Sheets

(51) Int. Cl.

| | |
|---|---|
| *C12M 1/12* | (2006.01) |
| *C12M 1/34* | (2006.01) |
| *C12M 3/00* | (2006.01) |
| *C12N 5/071* | (2010.01) |
| *C12N 5/077* | (2010.01) |

(52) U.S. Cl.
CPC ............ *C12M 29/10* (2013.01); *C12M 41/26* (2013.01); *C12M 41/40* (2013.01); *C12N 5/0656* (2013.01); *C12N 5/0688* (2013.01); *C12N 5/069* (2013.01); *C12N 2531/00* (2013.01); *C12N 2533/90* (2013.01)

(56) References Cited

U.S. PATENT DOCUMENTS

| | | | |
|---|---|---|---|
| 2015/0253309 A1* | 9/2015 | Marx ..................... | C12M 23/16 |
| | | | 435/284.1 |
| 2016/0313306 A1* | 10/2016 | Ingber ................... | C12M 21/08 |

FOREIGN PATENT DOCUMENTS

| | | | |
|---|---|---|---|
| JP | 2018-038425 | A | 3/2018 |
| JP | 2018-531603 | A | 11/2018 |
| KR | 10-2019-0028810 | A | 3/2019 |
| KR | 10-2019-0035524 | A | 4/2019 |
| KR | 10-2019-0088711 | A | 7/2019 |
| WO | 2010/009307 | A2 | 1/2010 |
| WO | 2013085909 | A1 | 6/2013 |
| WO | 2017096285 | A1 | 6/2017 |
| WO | 2017096297 | A1 | 6/2017 |
| WO | 2018102201 | A1 | 6/2018 |

OTHER PUBLICATIONS

Zacharias, William et al.; "Isolation and culture of human alveolar epithelial progenitor cells"; Protocol Exchange; Jun. 11, 2018; 9 pages.

"International Search Report"; prepared for application No. PCT/KR2020/013365; Jan. 21, 2021; 9 pages.

Khalid Muhammad Asad Ullah et al: "A lung cancer-on-chip platform with integrated biosensors for physiological monitoring and toxicity assessment", Biochemical Engineering Journal, Elsevier, Amsterdam, NL, vol. 155, Dec. 16, 2019.

Li Kaiyan et al: "Biomimetic human lung-on-a-chip for modeling disease investigation", Materials Genome Institute, Shanghai University 1 , Shanghai 200444, China, vol. 13, No. 3, May 1, 2019.

* cited by examiner

MICROFLUIDIC SYSTEM SIMULATING LUNG TISSUE

TECHNICAL FIELD

The present specification discloses a microfluidic system simulating a lung tissue which includes lung epithelial cells and lung fibroblasts which are isolated from human lungs and commercially available vascular endothelial cells, and in which microfluid is perfused, a method for manufacturing the same, and a microfluidic control method using the same.

[National R&D Project Supporting the Present Invention]
[Project Identification Number] 16C1787
[Name of Ministry] Ministry of Health and Welfare
[Specialized Institution for Research and Management]
The Korea Health Industry Development Institute
[Research Business Title] Development of Technology to Overcome Disease
[Research Project Title] Clinical Efficacy Study of Acute Lung Injury New Drug Candidates Based on Biomimetic Chips
[Contribution Rate] 1/1
[Organizer] Seoul National University Bundang Hospital
[Period of Research] Jul. 1, 2016 to Aug. 31, 2019

BACKGROUND ART

The lung is an essential organ responsible for respiration and is an organ that obtains oxygen and releases carbon dioxide through inhalation and exhalation of air. Red blood cells in the blood, which pass through the capillaries of the alveoli where gas exchange takes place in the lung, transport carbon dioxide produced in the body, then release the carbon dioxide out of the body through the alveoli, take oxygen from the atmosphere, and transport oxygen throughout the body. Therefore, unlike other organs in the human body, gas flows in and out in the lung.

Meanwhile, in-vivo and in-vitro models for the study of lung diseases are still not sufficiently developed due to the characteristics of the lung. For example, animal models often do not develop pathological abnormalities of the airways and lungs as found in humans, and most in-vitro models cannot reproduce the tissue components and the structural complexity of actually variously differentiated airway epithelial cells. Further, as described above, in-vitro models simulating the lungs should be exposed to the gas containing oxygen for the study. However, if in-vitro models manufactured using commercially available cells are exposed to the gas, cells die, for example, within three days, and thus the in-vitro models are not appropriate for a series of processes of model production, drug effect exploration, drug toxicity screening, and the like, which take at least seven days or longer.

Accordingly, the present inventors have conducted a study on a microfluidic system in which cells survive for a long period of time even while the gas and the medium-containing fluid is perfused, so that simulation of various lung disease models, efficacy test for therapeutic drugs, other harmful substance tests, in-vitro diagnosis, and personalized medicine prescription are enabled, and have completed the present invention.

DISCLOSURE

Technical Problem

According to an aspect, an object of the present invention is to provide a microfluidic system simulating a lung tissue which includes lung epithelial cells and lung fibroblasts, which are isolated from a human lung, and commercially available vascular endothelial cells, and where a gas and a medium-containing fluid are perfused inside the system, and a pH sensor and a $pO_2$ sensor which senses partial oxygen pressure ($pO_2$) among gas partial pressures are included.

According to another aspect, an object of the present invention is to provide a method of manufacturing the microfluidic system simulating a lung tissue.

According to another aspect, an object of the present invention is to provide a method of monitoring a cell culture environment in the microfluidic system simulating a lung tissue, which includes a step of perfusing a microfluid to the microfluidic system simulating a lung tissue and measuring pH and $pO_2$.

Solution to Problem

According to an aspect, the present invention provides a microfluidic system simulating a lung tissue, the system including a first layer; a second layer; a third layer; a first chamber for gas perfusion between the first layer and the second layer; and a second chamber for medium-containing fluid perfusion between the second layer and the third layer, in which the second layer may include a porous membrane, the porous membrane may include lung epithelial cells, lung fibroblasts, and commercially available vascular endothelial cells (human umbilical vein endothelial cells), the lung epithelial cells may face the first chamber, the vascular endothelial cells may face the second chamber, the lung fibroblasts may be present between the vascular endothelial cells and the lung epithelial cells, the lung epithelial cells and the lung fibroblasts may be cells isolated from a human lung, and the first layer and the third layer may include one or more pH sensors and one or more gas $pO_2$ sensors, respectively.

According to another aspect, the present invention provides a method for manufacturing the microfluidic system simulating a lung tissue, including a step (1) of coating a porous membrane of a second layer with an extracellular matrix; a step (2) of seeding and culturing lung epithelial cells isolated from a human on the coated porous membrane; and a step (3) of seeding and culturing lung fibroblasts isolated from a human and the commercially available vascular endothelial cells (human umbilical vein endothelial cells) on an opposite surface of the porous membrane on which the lung epithelial cells are seeded.

In addition, according to another aspect, the present invention provides a method of monitoring a cell culture environment in the microfluidic system simulating a lung tissue, the method including a microfluidic perfusion step of perfusing gas to the first chamber of the microfluidic system simulating a lung tissue and perfusing the medium-containing fluid to the second chamber; and a step of measuring pH by the pH sensor of the system and measuring $pO_2$ by the $pO_2$ sensor.

Advantageous Effects of the Invention

The present invention relates to a microfluidic system simulating a lung tissue including lung epithelial cells and lung fibroblasts isolated directly from human lungs, in which a gas and a medium-containing fluid may be perfused in each chamber inside the system, and all the three types of cells in the system may survive even when a week or more have elapsed after the perfusion of the gas and the fluid. In addition, oxygen delivery and pH may be monitored by using the pH sensor and the pO$_2$ sensor inside the system, and thus whether the three types of cells in the system are growing in the same environment as in the lungs in vivo may be confirmed. Therefore, by the microfluidic system simulating a lung tissue according to an aspect of the present invention using a human, particularly a lung of a lung-injured patient, a wide range of studies including the implementation of a lung disease model, a test for therapeutic drug efficacy, and other harmful substance tests may be performed, and further, in-vitro diagnosis, personalized medicine prescription, and the like may be performed.

BRIEF DESCRIPTION OF DRAWINGS

FIGS. 9a to 9c are schematic views showing seeding of lung epithelial cells and lung fibroblasts isolated from a human and commercially available vascular endothelial cells on a porous membrane of a middle layer of the system during a process of preparing a microfluidic system simulating a lung tissue according to an example of the present

Figure 9A:
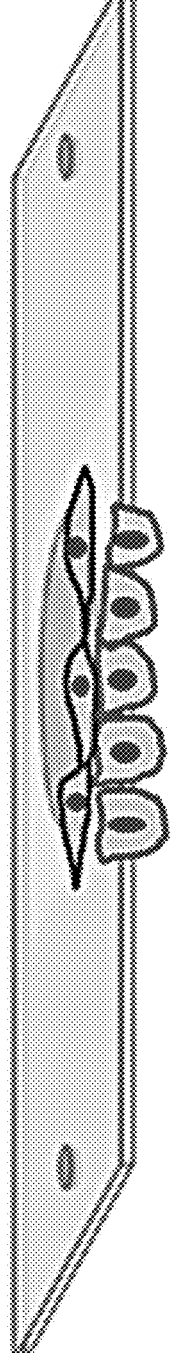
Figure 9B:
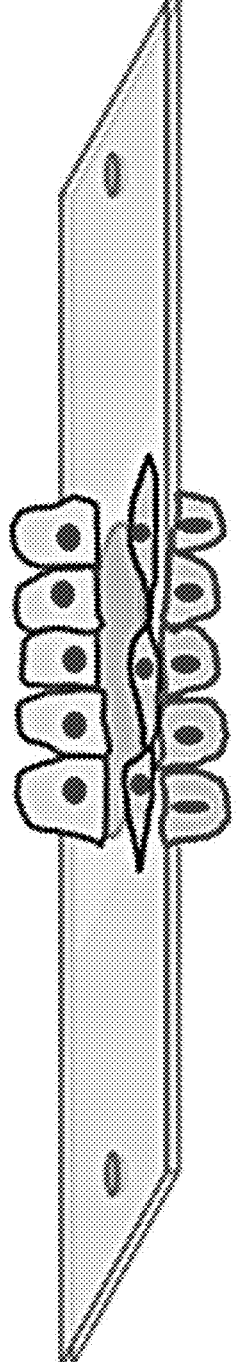
Figure 9C:
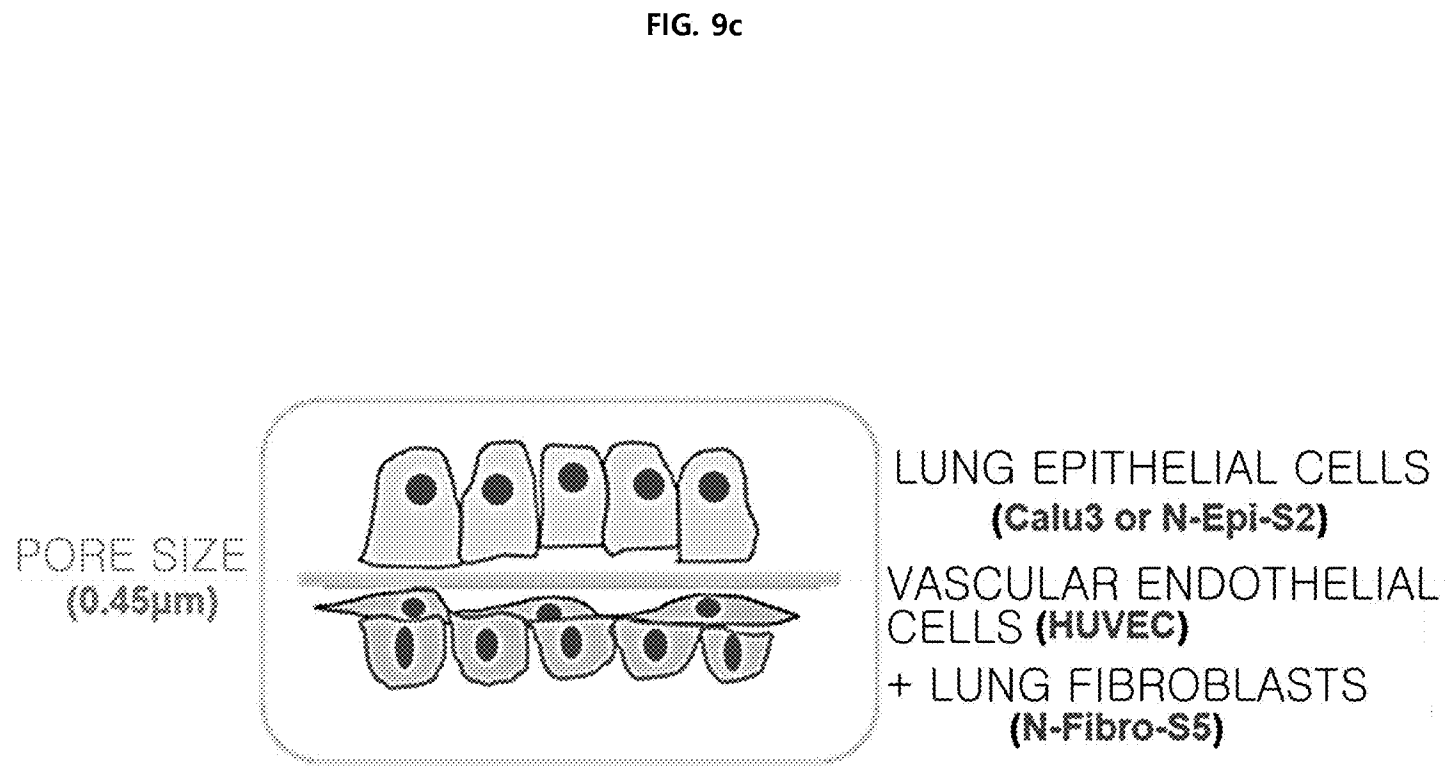

4 invention. FIG. 9a is a view schematically showing results of seeding and then culturing lung fibroblasts and vascular endothelial cells, FIG. 9b is a diagram schematically showing results of seeding and then culturing lung epithelial cells, and FIG. 9c is a view schematically showing results of seeding and culturing all three types of cells and then attaching the cells to a porous membrane of a middle layer.

Figure 10A:
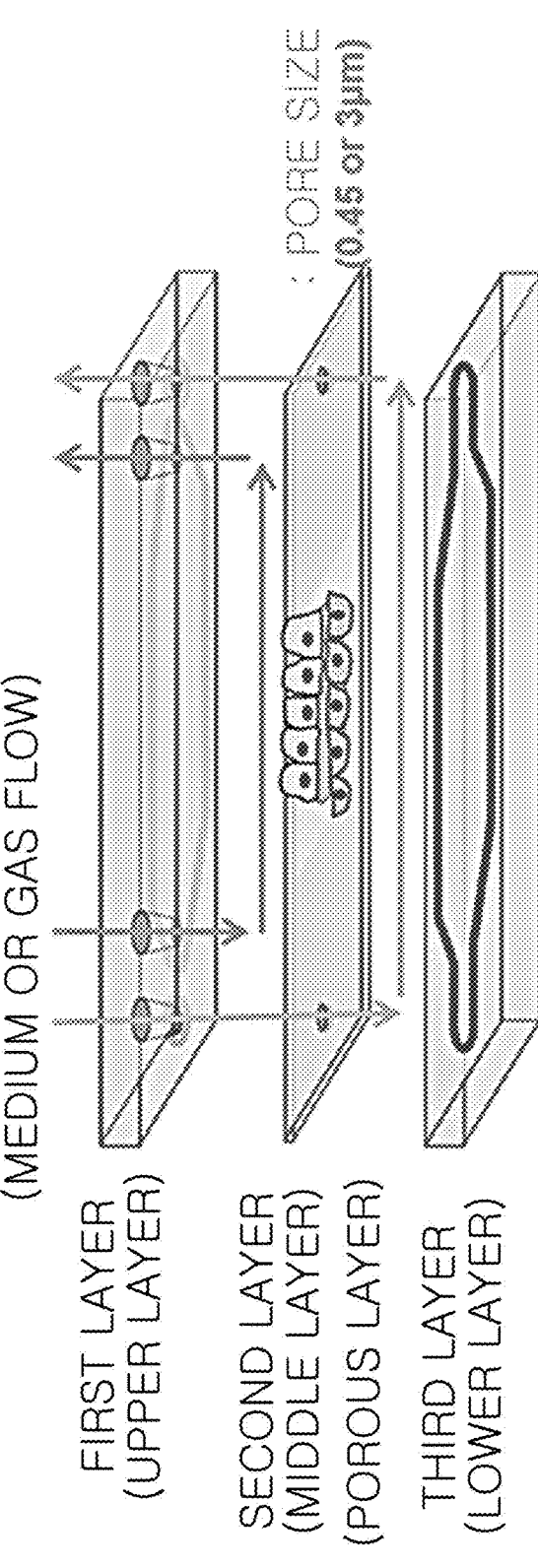
Figure 10B:
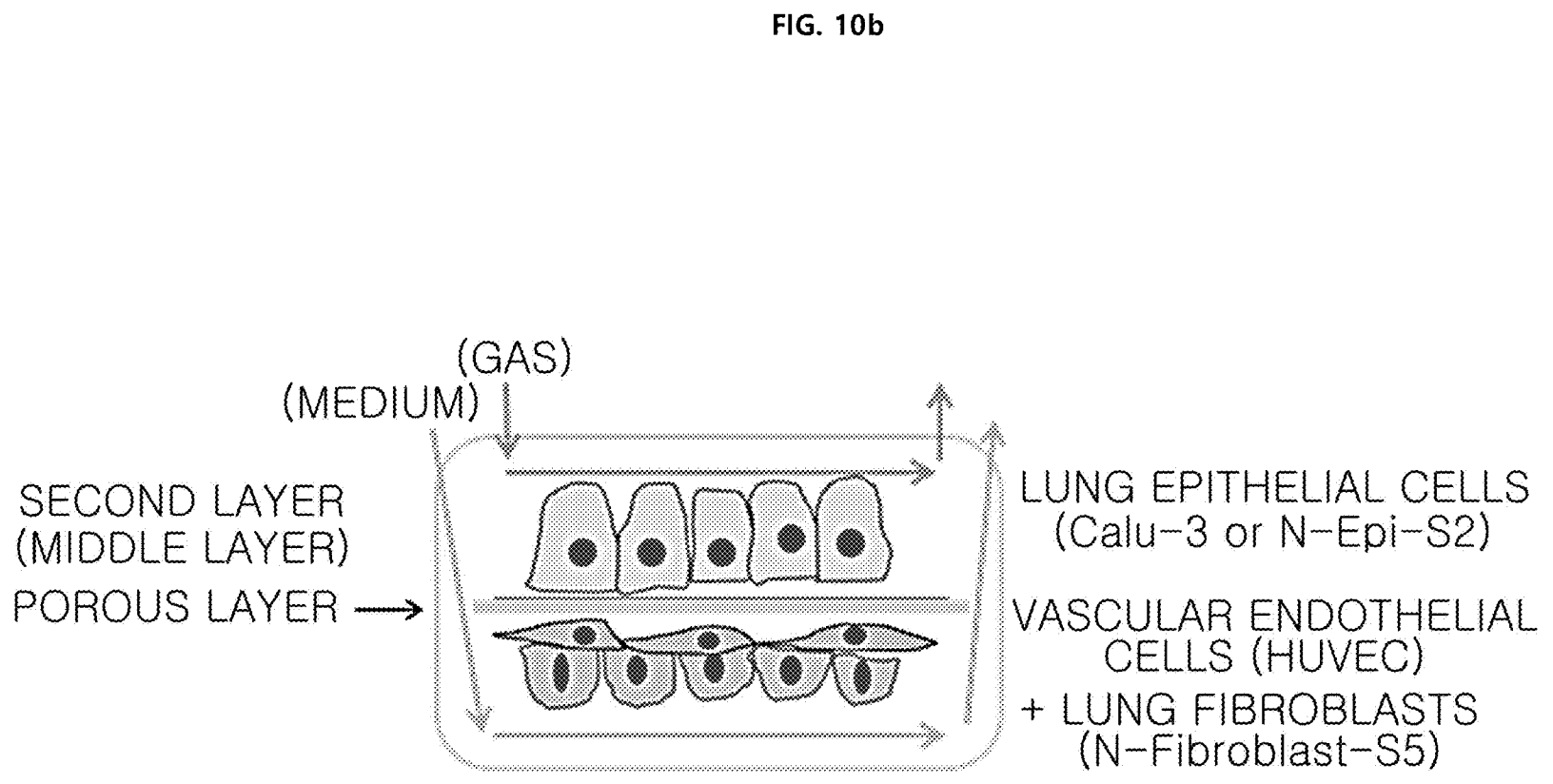

FIG. 10a is a view schematically showing a state in which a fluid is administered to a microfluidic system simulating a lung tissue according to an example of the present invention, and FIG. 10b is a view more specifically showing a porous membrane portion of a middle layer containing the three types of cells in the system.

Figure 11:
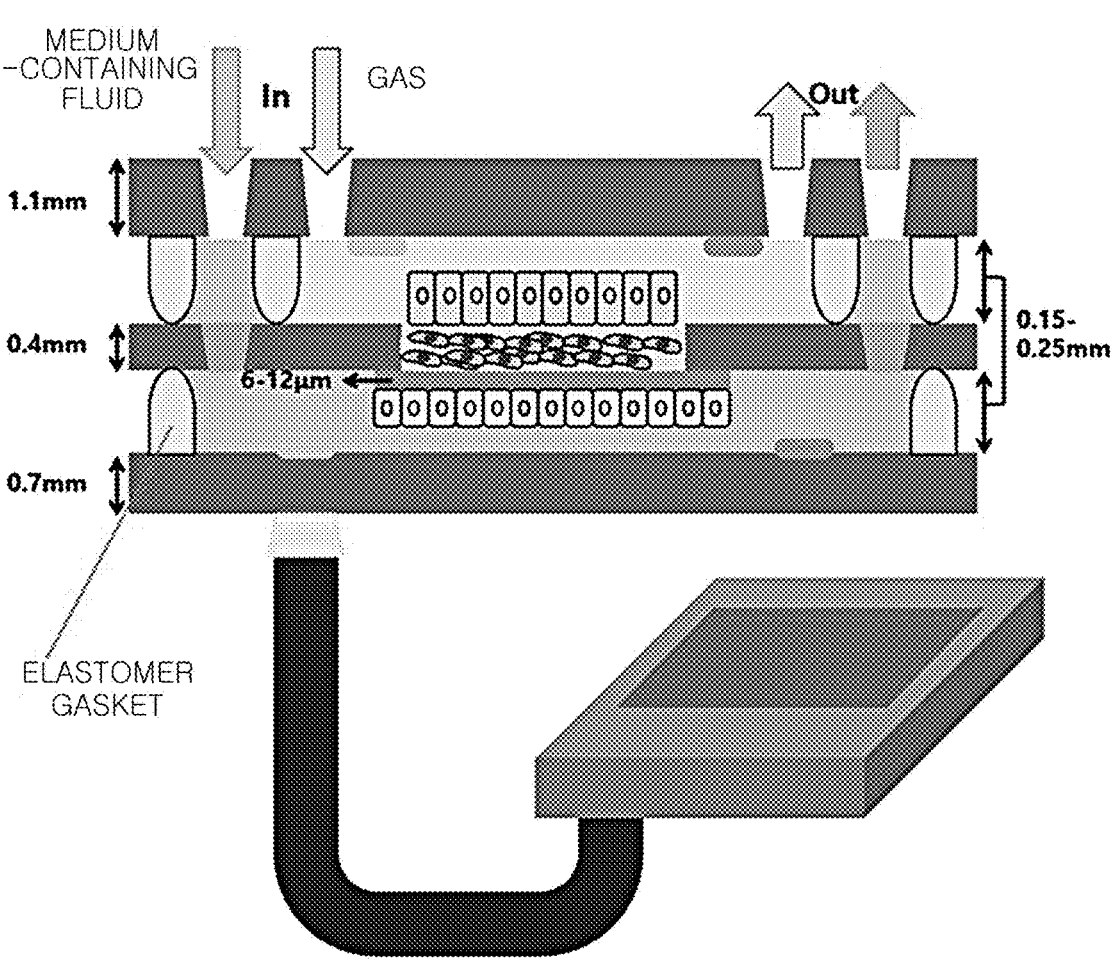

FIG. 11 is a view showing a process of reading an actual sensor value in a microfluidic system simulating a lung tissue to which a pH sensor and a pO$_2$ sensor are attached, according to an example of the present invention.

FIGS. 12a to 12d are views showing results of immunofluorescence analysis when four days elapse after the medium-containing fluid are perfused inside a microfluidic system simulating a lung tissue according to an example of the present invention.

Figure 12A:
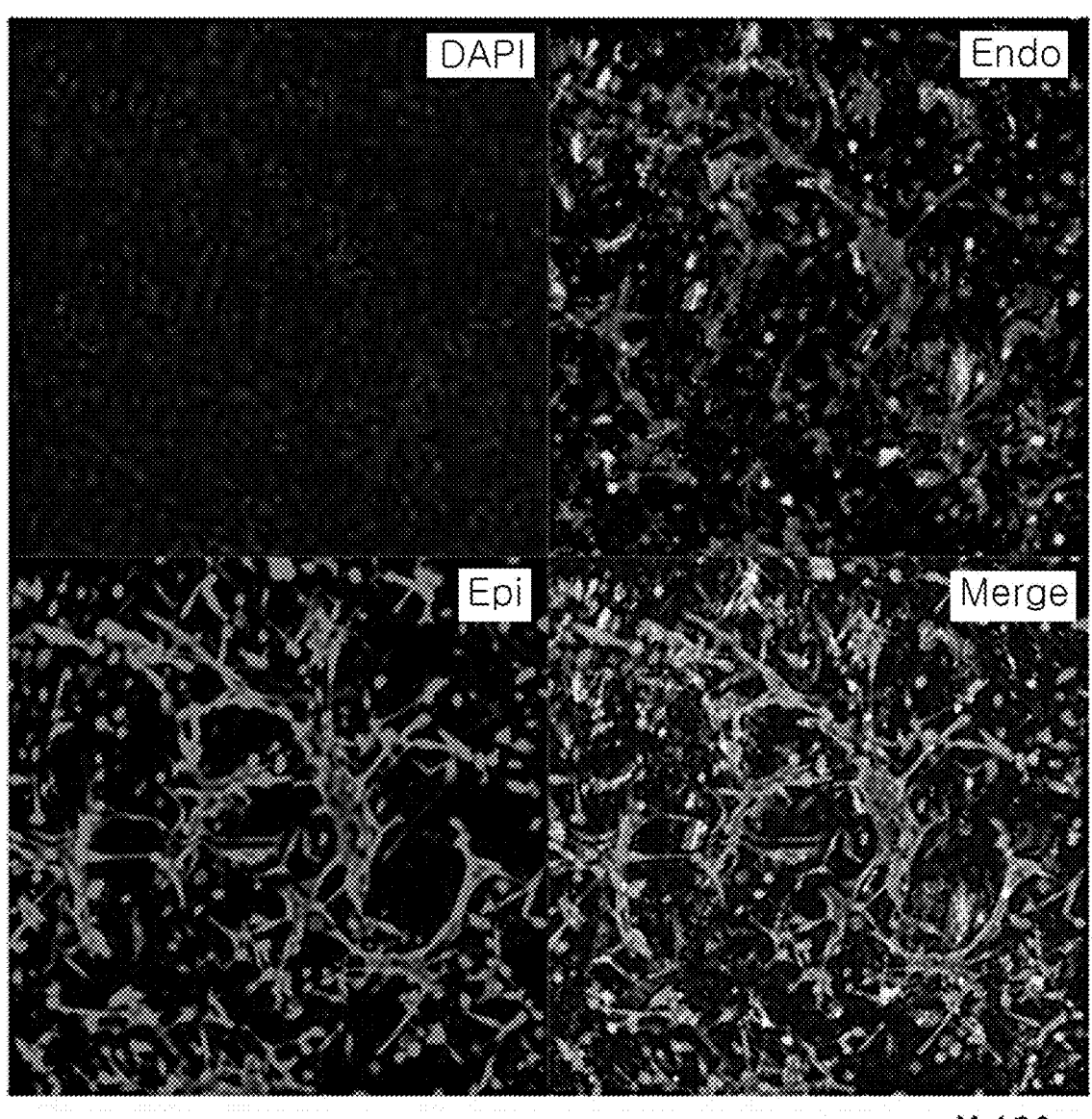
Figure 12B:
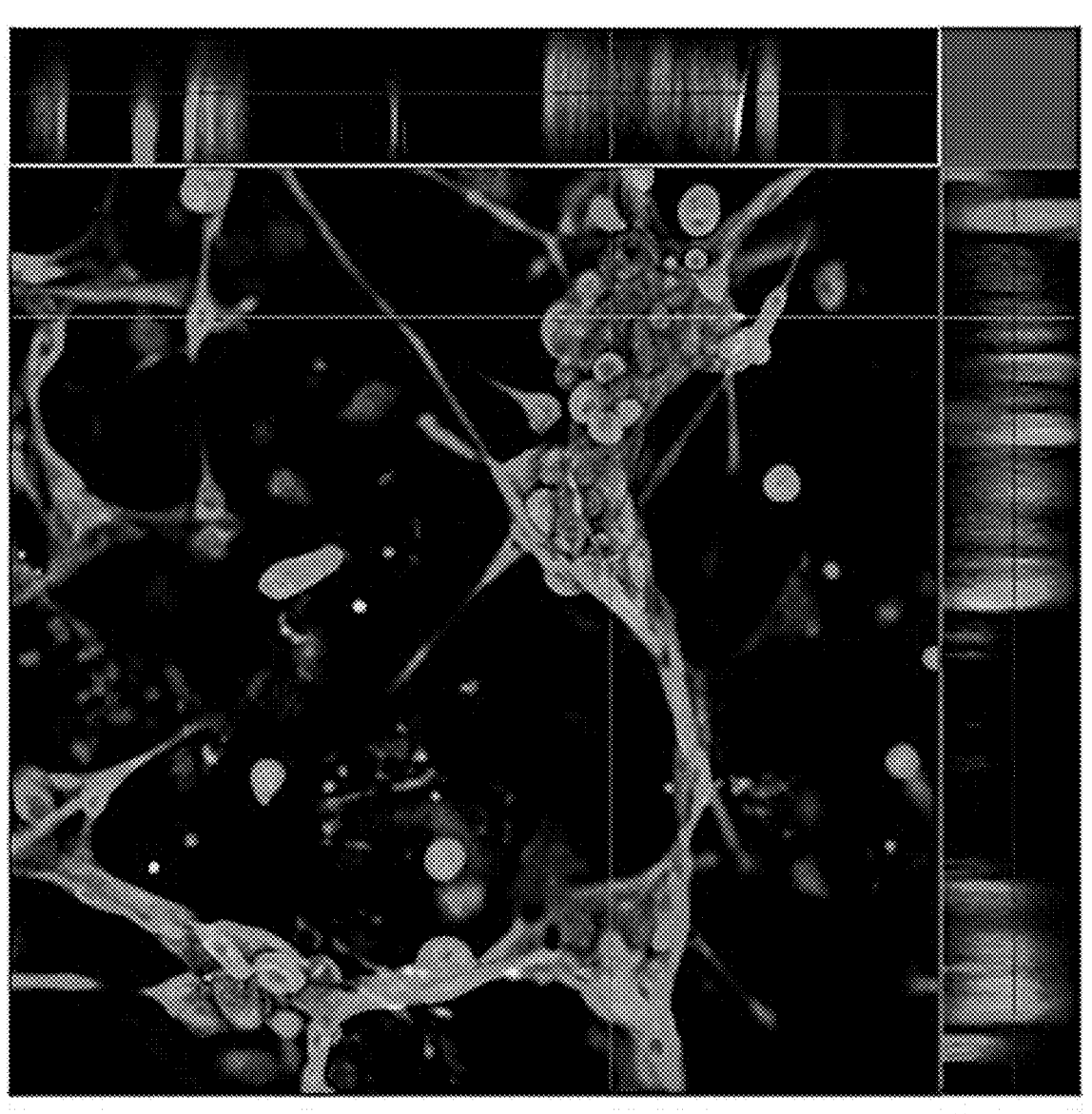
Figure 12C:
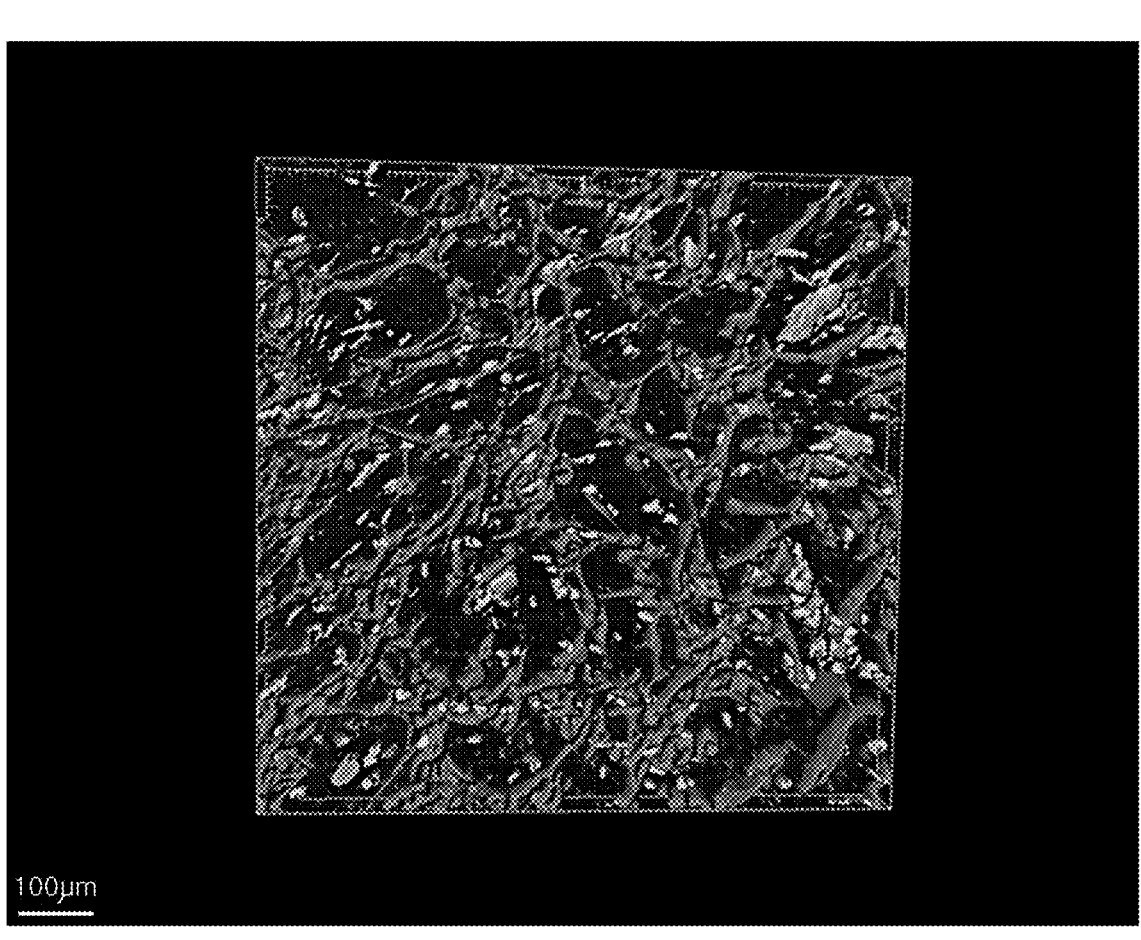
Figure 12D:
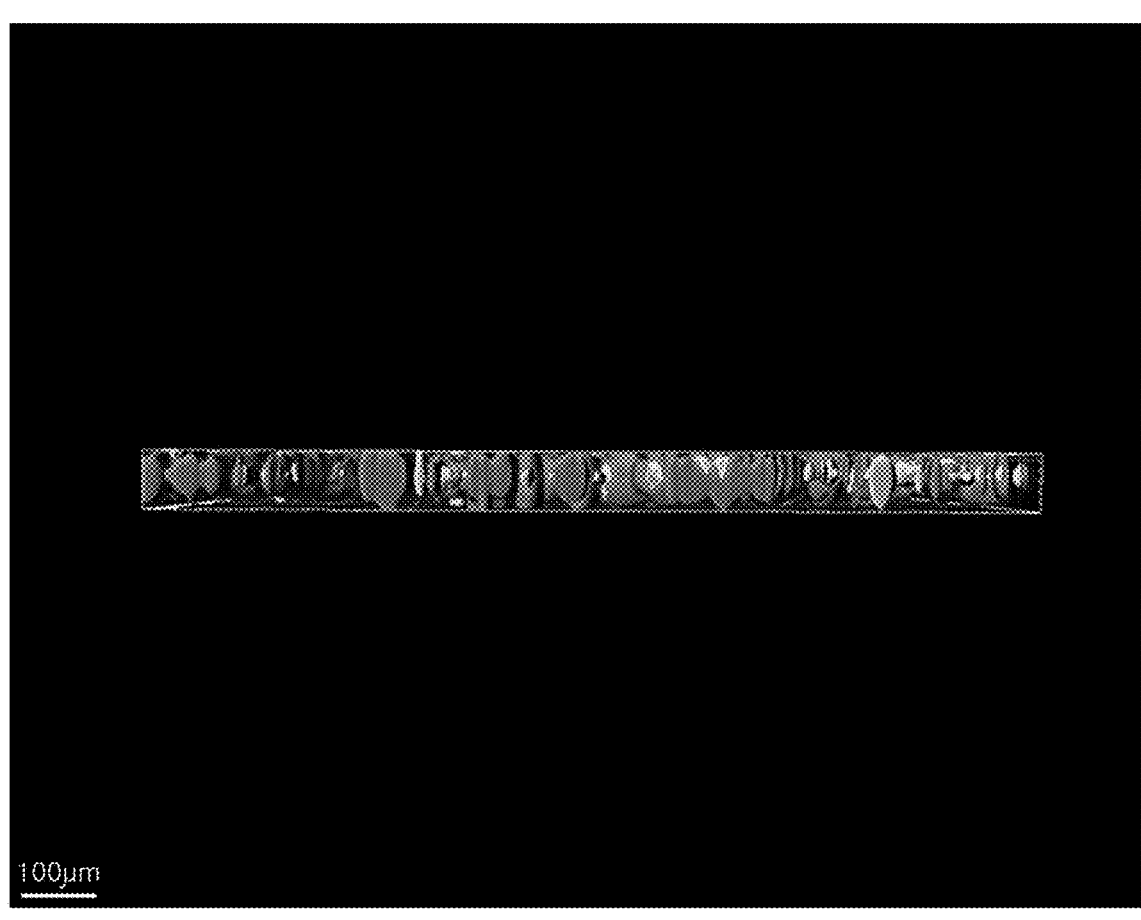

In FIGS. 12a to 12d, the red color (Epi) indicates lung epithelial cells, and the green color (Endo) indicates vascular endothelial cells. FIG. 12a shows results confirmed by co-culturing epithelial cells and endothelial cells and then staining the epithelial cells in red and the endothelial cells in green. FIG. 12b is a result obtained by observing a side cell shape after co-culture, in Ortho format under a confocal microscope. FIG. 12c shows a result extracted from a video reconstructed in three dimensions with pictures taken with a confocal microscope by using the Imaris program and shows that the co-culture is well formed. FIG. 12d is an image obtained by checking the video of FIG. 12c from a side.

Figure 13A:
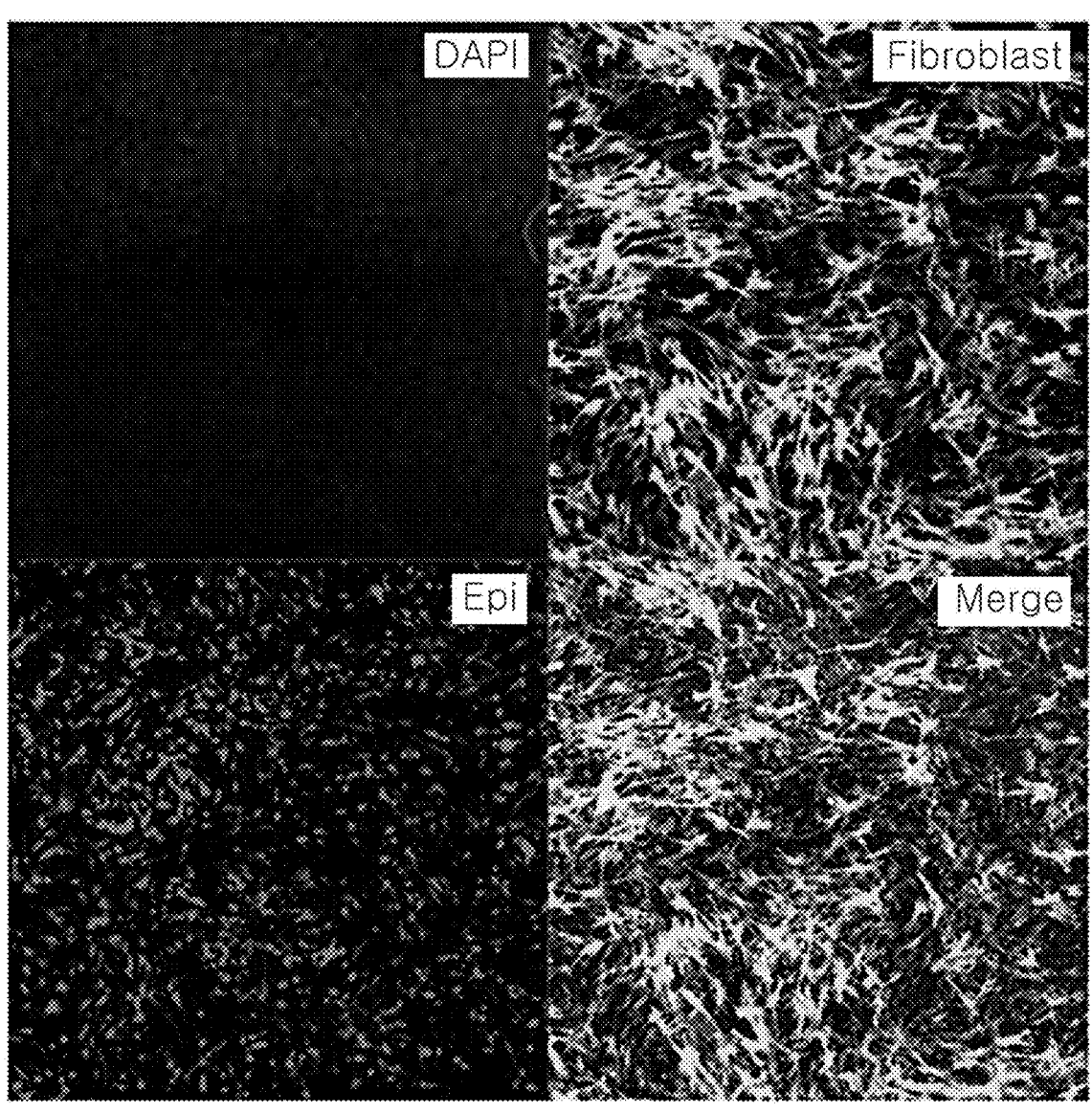
Figure 13B:

FIGS. 13a and 13b are views showing results of immunofluorescence analyses when two days elapse after the gas and the medium-containing fluid are perfused inside a microfluidic system simulating a lung tissue according to an example of the present invention. In FIGS. 13a and 13b, the green color (Fibroblast) indicates lung fibroblasts, and the red color (Epi) indicates lung epithelial cells.

Figure 14A:
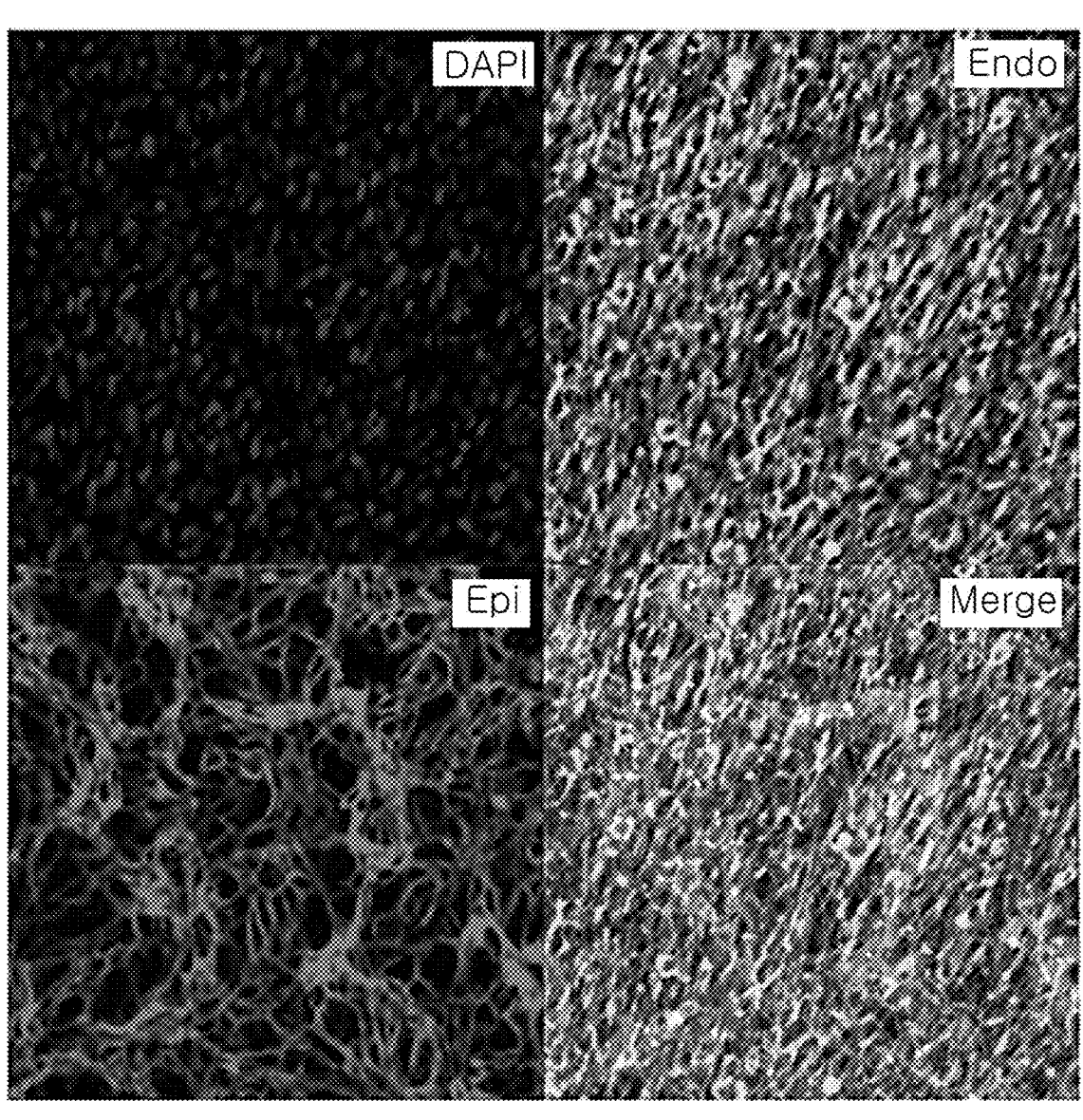
Figure 14B:
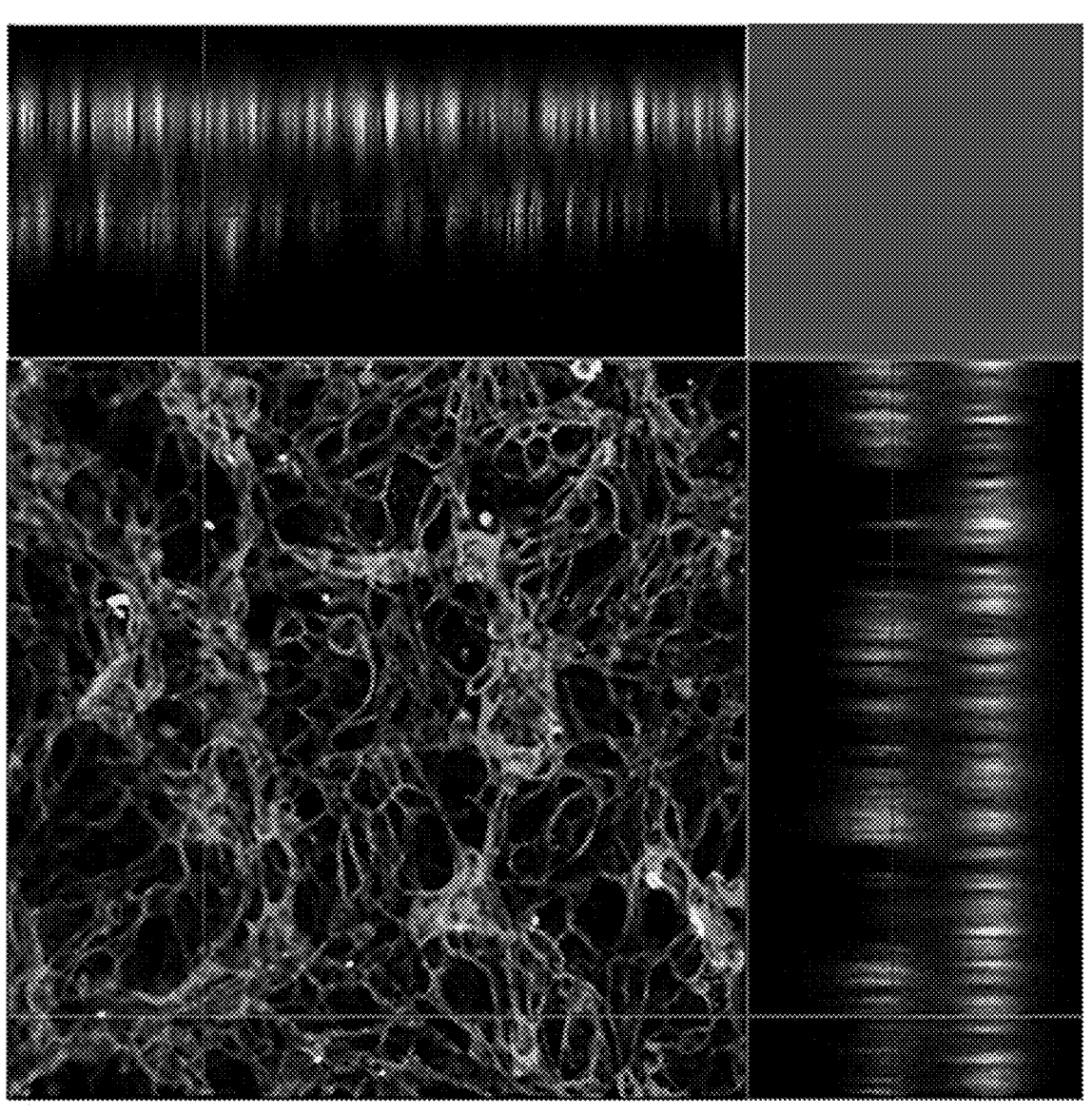
Figure 14C:
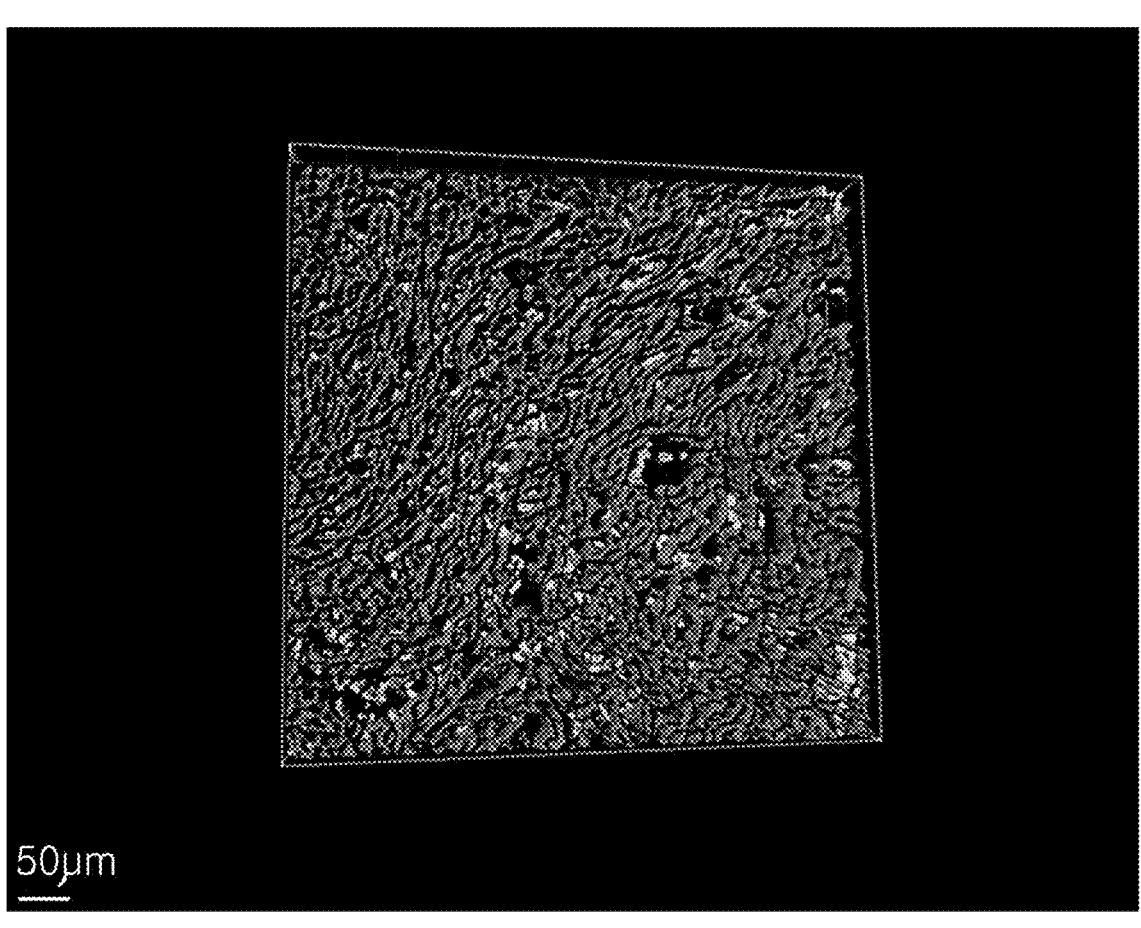
Figure 14D:
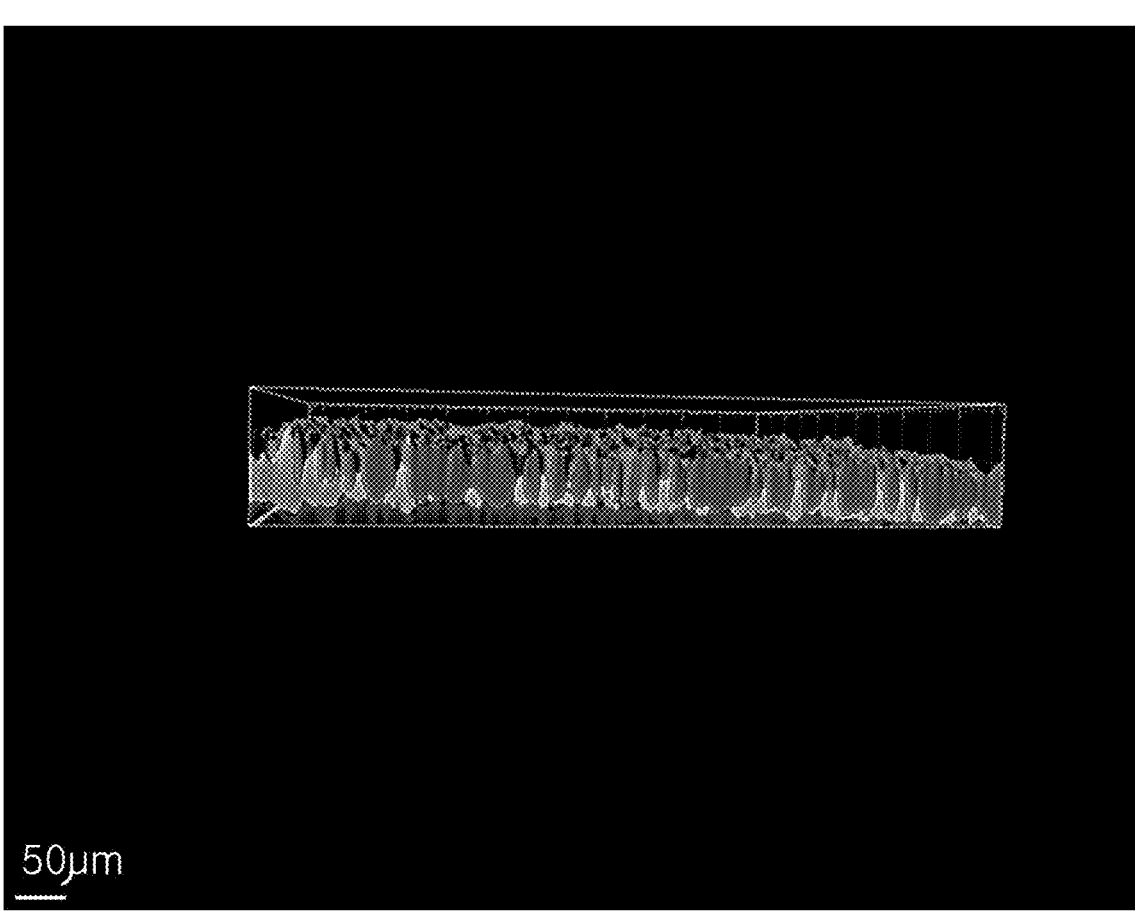
Figure 14E:
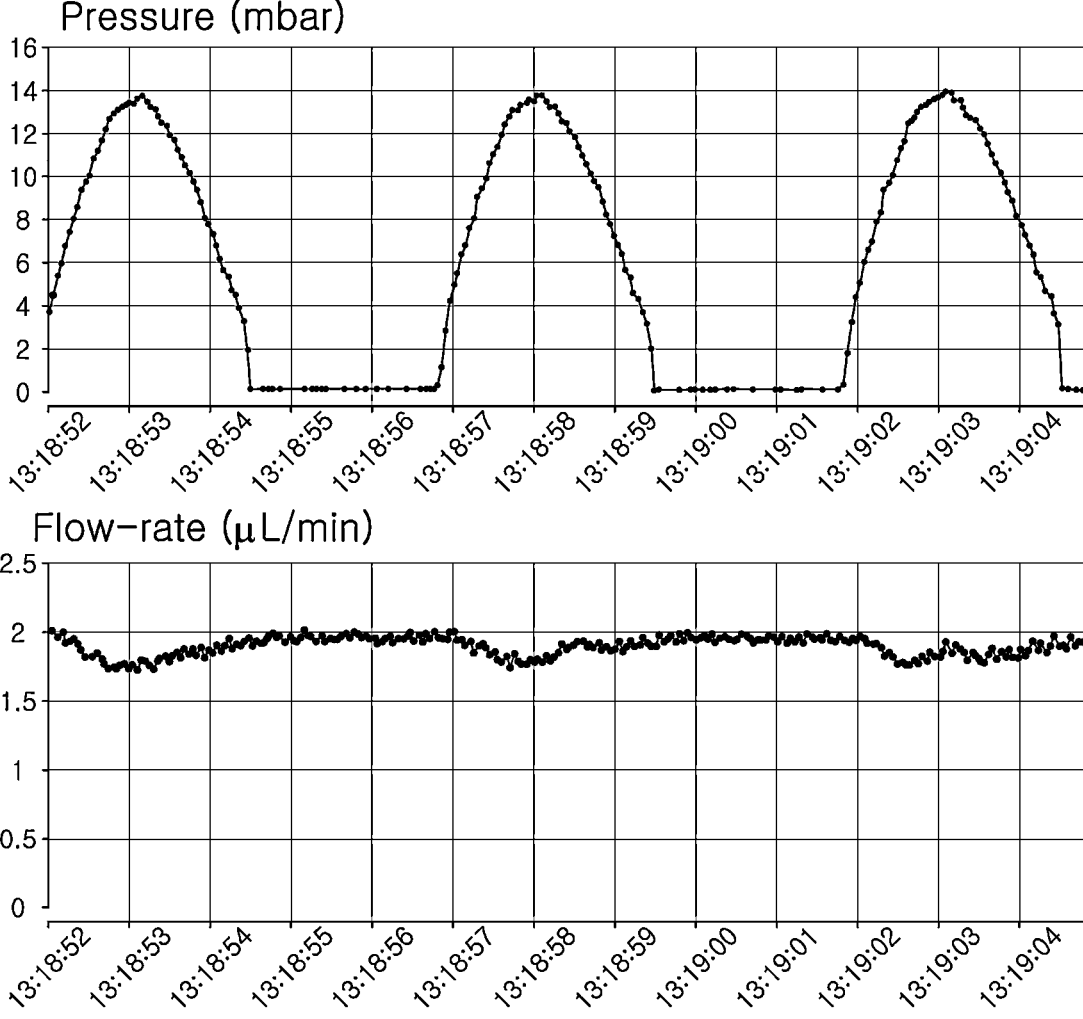
Figure 14F:
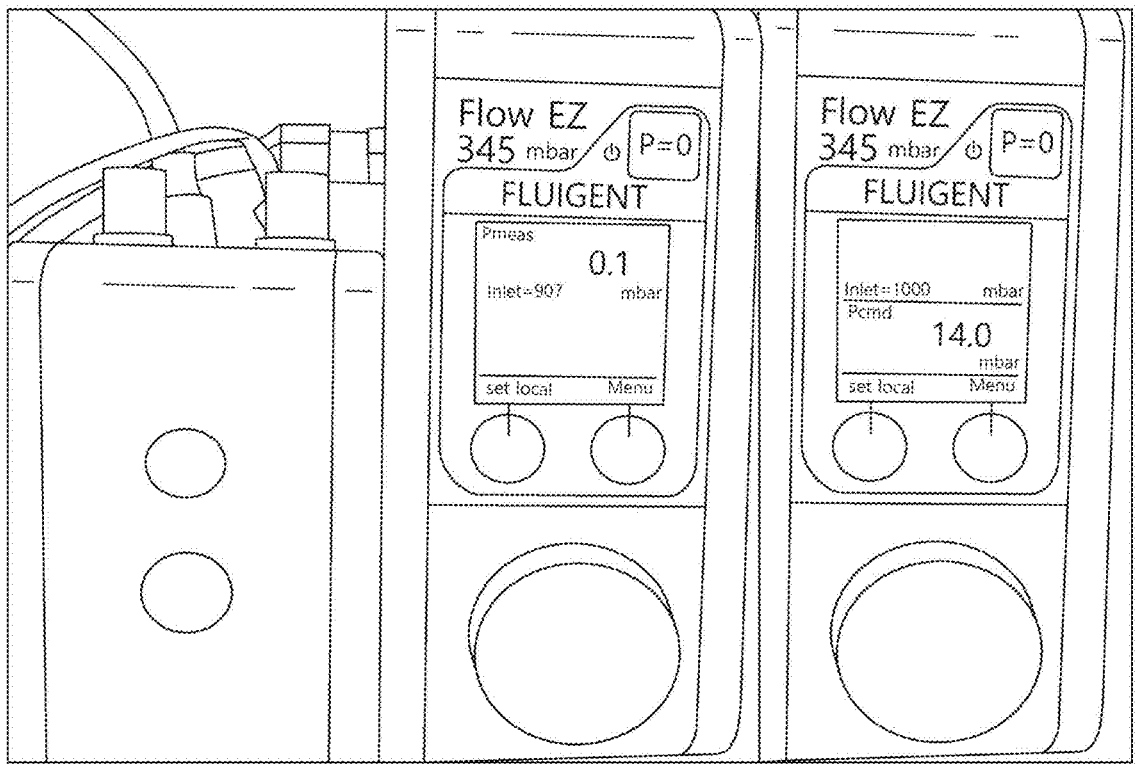

FIGS. 14a to 14d are views showing results of immunofluorescence analyses when four days elapse after the gas and the medium-containing fluid are perfused inside a microfluidic system simulating a lung tissue according an example of the present invention. In FIGS. 14a to 14c, the red color (Epi) indicates lung epithelial cells, and the green color (Endo) indicates vascular endothelial cells. FIG. 14a shows the results confirmed by co-culturing the epithelial cells (Calu3) and the endothelial cells (Endo) and staining the epithelial cells in red and the endothelial cells in green. FIG. 14b is a result obtained by observing a side cell shape after co-culture, in an Ortho format under a confocal microscope. FIG. 14c is a result extracted from a video reconstructed in three dimensions with pictures taken with a confocal microscope by using the Imaris program and shows that the co-culture is well formed. FIG. 14d is an image obtained by checking the video of FIG. 14c from a side. FIG. 14e is a graph showing a state of simulating a respiration movement when the actual gas is perfused, and FIG. 14f is an apparatus for simulating and measuring the corresponding respiration movement.

Figure 15A:
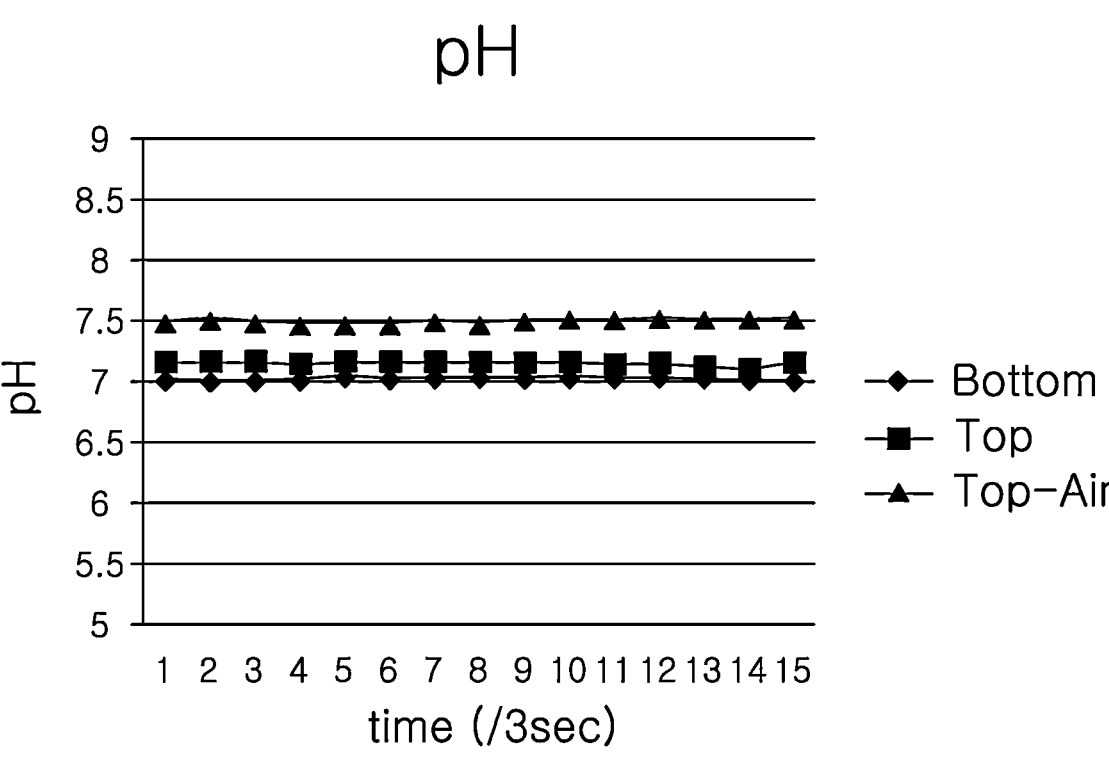
Figure 15B:
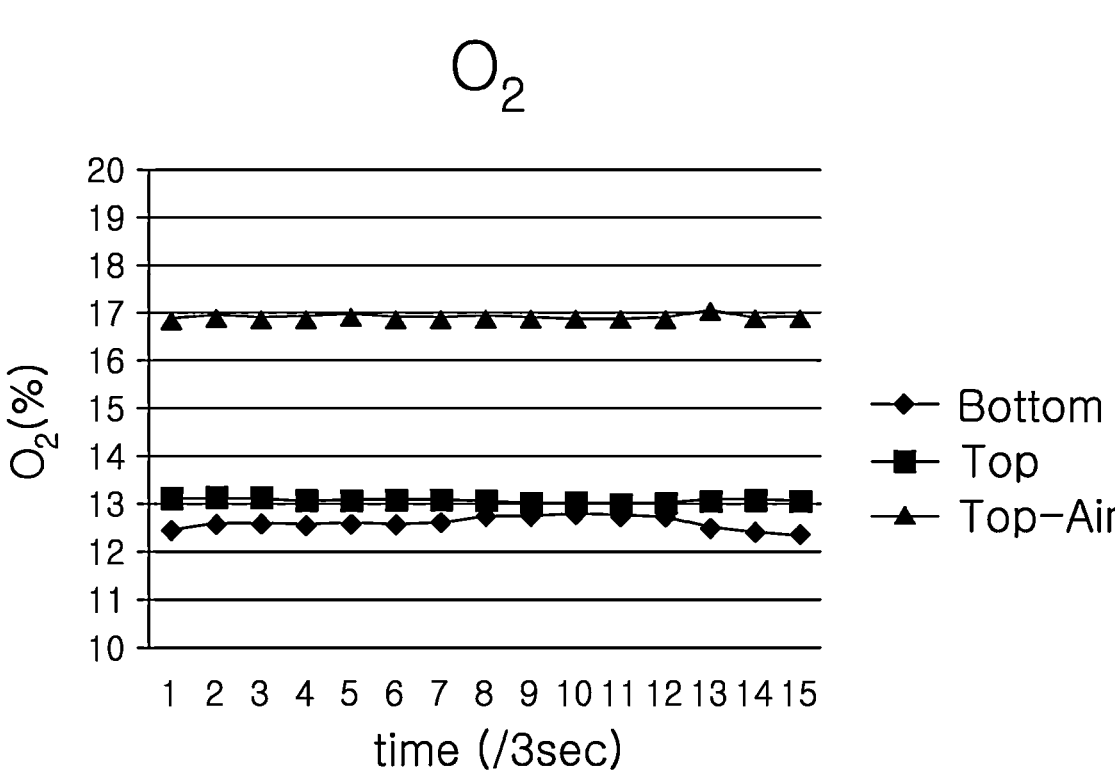

FIGS. 15a and 15b are views showing results obtained by perfusing the fluid inside a microfluidic system simulating a lung tissue according to an example of the present invention and measuring pH (FIG. 15a) and pO$_2$ (FIG. 15b) by using an internal pH sensor and an internal pO$_2$ sensor.

MODE FOR INVENTION

Hereinafter, the present invention is described in detail.

In the present specification, the term "microfluid" refers to a minute fluid that is perfused inside a subject, specifically, may be a fluid that is perfused in a human lung, and more specifically, may be a gas, for example oxygen or carbon dioxide, that is perfused in a human lung, may be blood, lymph, or the like that is perfused in blood vessels forming a human lung, and a fluid other than gas, such as blood, may be replaced with a medium-containing fluid in vitro.

According to an aspect, the present invention provides a microfluidic system simulating a lung tissue, which may include a first layer, a second layer, a third layer, a first chamber for gas perfusion between the first layer and the second layer, and a second chamber for medium-containing fluid perfusion between the second layer and the third layer, in which the second layer may include a porous membrane, the porous membrane may include lung epithelial cells, lung fibroblasts, and vascular endothelial cells (human umbilical vein endothelial cells), the lung epithelial cells may face the first chamber, the vascular endothelial cells may face the second chamber, the lung fibroblasts may be present between the vascular endothelial cells and the lung epithelial cells, the lung epithelial cells and the lung fibroblasts may be isolated from a human lung, and the first layer and the third layer may include one or more pH sensors and one or more gas partial pressure sensors, respectively.

According to an aspect of the present invention, the microfluidic system simulating a lung tissue may include a first layer, a second layer, and a third layer, may include a first chamber between the first layer and the second layer, and may include a second chamber between the second layer and the third layer. The first chamber does not indicate an additional configuration for configuring the same, but means a space formed by the presence of the first layer and the second layer, and the first chamber is used for gas perfusion. The second chamber also does not indicate an additional configuration for configuring the same, but means a space formed by the presence of the second layer and the third layer, and the second chamber is used for perfusing a medium-containing fluid.

According to an aspect of the present invention, the first layer, the second layer, and the third layer each may be glass including one or more selected from the group consisting of silicate, borosilicate, and phosphate, and specifically, the first layer, the second layer, and the third layer each may be borosilicate glass, but are not limited thereto. Materials configuring the first layer, the second layer, and the third layer may be the same or may be different from each other.

According to an aspect of the present invention, the thicknesses of the first layer, the second layer, and the third layer each may be 0.1 to 2 mm, specifically, may be 0.1 mm or more, 0.2 mm or more, 0.3 mm or more, 0.4 mm or more, 0.5 mm or more, 0.6 mm or more, 0.7 mm or more, 0.8 mm or more, 0.9 mm or more, 1.0 mm or more, 1.1 mm or more, 1.2 mm or more, 1.3 mm or more, 1.4 mm or more, 1.5 mm or more, 1.6 mm or more, 1.7 mm or more, 1.8 mm or more, or 1.9 mm or more, and may be 2.0 mm or less, 1.9 mm or less, 1.8 mm or less, 1.7 mm or less, 1.6 mm or less, 1.5 mm or less, 1.4 mm or less, 1.3 mm or less, 1.2 mm or less, 1.1 mm or less, 1.0 mm or less, 0.9 mm or less, 0.8 mm or less, 0.7 mm or less, 0.6 mm or less, 0.5 mm or less, 0.4 mm or less, 0.3 mm or less, or 0.2 mm or less, but the thicknesses are not limited thereto. The thicknesses of the first layer, the second layer, and the third layer may be the same or may be different from each other.

According to an aspect of the present invention, the second layer may include a porous membrane. A material that configure the porous membrane may be a polymer, and the polymer may be one or more selected from the group consisting of polyethylene terephthalate (PET), polydimethylsiloxane (PDMS), polycarprolactone (PCL), and nanofiber, but is not limited thereto. The thickness of the porous membrane may be 3 to 24 $\mu$m, specifically, may be 3 $\mu$m or more, 4 $\mu$m or more, 6 $\mu$m or more, 7 $\mu$m or more, 8 $\mu$m or more, 9 $\mu$m or more, 10 $\mu$m or more, 11 $\mu$m or more, 12 $\mu$m or more, 14 $\mu$m or more, 16 $\mu$m or more, 18 $\mu$m or more, 20 $\mu$m or more, or 22 $\mu$m or more, and may be 24 $\mu$m or less, 22 $\mu$m or less, 20 $\mu$m or less, 18 $\mu$m or less, 16 $\mu$m or less, 14 $\mu$m or less, 12 $\mu$m or less, 11 $\mu$m or less, 10 $\mu$m or less, 9 $\mu$m or less, 8 $\mu$m or less, 7 $\mu$m or less, 6 $\mu$m or less, or 4 $\mu$m or less, but is not limited thereto, and may differ depending on the size of the microfluidic system simulating a lung tissue, the second layer, or the porous membrane. A pore size of the porous membrane may be 1 to 16 $\mu$m, specifically, may be 1 $\mu$m or more, 2 $\mu$m or more, 3 $\mu$m or more, 4 $\mu$m or more, 5 $\mu$m or more, 6 $\mu$m or more, 7 $\mu$m or more, 8 $\mu$m or more, 9 $\mu$m or more, 10 $\mu$m or more, 11 $\mu$m or more, 12 $\mu$m or more, 13 $\mu$m or more, 14 $\mu$m or more, or 15 $\mu$m or more, and may be 16 $\mu$m or less, 15 $\mu$m or less, 14 $\mu$m or less, 13 $\mu$m or less, 12 $\mu$m or less, 11 $\mu$m or less, 10 $\mu$m or less, 9 $\mu$m or less, 8 $\mu$m or less, 7 $\mu$m or less, 6 $\mu$m or less, 5 $\mu$m or less, 4 $\mu$m or less, 3 $\mu$m or less or 2 $\mu$m or less, but is not limited thereto, and may differ depending on the size of the microfluidic system simulating a lung tissue, the second layer, or the porous membrane. The porous membrane may be coated with an extracellular matrix (ECM) so that the lung epithelial cells, the lung fibroblasts, or the vascular endothelial cells may be attached to the porous membrane, the extracellular matrix may be one or more selected from the group consisting of laminin, collagen type I, collagen type II, collagen type III, collagen type IV, collagen type V, collagen type VI, integrin, entactin, fibronectin, elastin, proteoglycan, vitronectin, poly-D-lysine, polysaccharide, and gelatin, but is not limited thereto as long as it can attach the lung epithelial cells, the lung fibroblasts, or the vascular endothelial cells to the porous membrane.

According to an aspect of the present invention, the porous membrane may include lung epithelial cells, the lung fibroblasts, and the vascular endothelial cells (human umbilical vein endothelial cells), and the lung epithelial cells and the lung fibroblasts may be isolated from a human lung. The lung epithelial cells and the lung fibroblasts may be obtained by an isolating method below including: a step of dissociating a lung tissue sample isolated from a human; a step of adding microbeads that specifically bind to the lung epithelial cells and microbeads that specifically bind to the lung fibroblast to the dissociated lung tissue sample; and a step of culturing the lung tissue sample bound with the added microbeads. In the isolating method, the microbeads that specifically bind to the lung epithelial cells may include cluster of differentiation 326 (CD326) and the microbeads that specifically bind to the lung fibroblasts may include anti-fibroblast microbeads. In this case, the lung epithelial cells and the lung fibroblasts each may be isolated by types from the human lung tissue sample in which various types of cells are mixed. In addition, if the gas and the medium-containing fluid is perfused in the microfluidic system simulating a lung tissue that includes the lung epithelial cells and the lung fibroblasts isolated from the human lung and the vascular endothelial cells, the cells are able to survive even when four, seven, or thirteen days elapsed (Experimental Example 1) unlike the single cell culture used in the related art, and to this end a wide range of studies including a drug efficacy test for a lung disease treatment and other harmful substance tests may be conducted, and further, in-vitro diagnoses, personalized medicine prescription, and the like are possible.

According to an aspect of the present invention, the lung epithelial cells may face the first chamber, the vascular endothelial cells may face the second chamber, and the lung fibroblasts may be present between the lung epithelial cells and the vascular endothelial cells. Owing to the positions of the lung epithelial cells and vascular endothelial cells as above, the lung epithelial cells may connect with the gas perfused in the first chamber and the vascular endothelial cells may connect with the medium-containing fluid perfused to the second chamber, so that the cells are able to be present in a microenvironment similar to an actual human lung.

According to an aspect of the present invention, the lung epithelial cells may be alveoli epithelial cells, and the alveoli epithelial cells may include type 1 alveoli epithelial cells and type 2 alveoli epithelial cells. The type 1 alveoli epithelial cells and the type 2 alveoli epithelial cells may be present in a ratio of 7:3 or 9:1, but is not limited thereto.

According to an aspect of the present invention, the first layer may include a first inlet through which a gas is injected, a first outlet through which the gas is discharged, a second inlet through which a medium-containing fluid is injected, and a second outlet through which the fluid is discharged, and the second layer may include two or more passages through which the medium-containing fluid is perfused from the first chamber to the second chamber. The numbers of the first inlets, the first outlets, the second inlets, and the second outlets may be one or more.

According to an aspect of the present invention, the first layer and the third layer may include one or more pH sensors, and one or more gas partial pressure sensors, respectively. Specifically, the first layer may include one or more pH sensors or one or more gas partial pressure sensors, and the third layer may include one or more pH sensors or one or more gas partial pressure sensors. More specifically, the first layer may include one or more gas partial pressure sensors, and the third layer may include one or more pH sensors. The pH sensor may be a sensor that measures pH inside the microfluidic system simulating a lung tissue, and may be a sensor that measures pH in the second chamber into which the medium-containing fluid injected through the second inlet is perfused. The gas partial pressure sensor may be a sensor that measures a partial oxygen pressure ($pO_2$) and may be a sensor that measures a partial oxygen pressure in the first chamber into which the gas injected through the first inlet is perfused. The pH sensor is a sensor that measures pH in real time, and the gas partial pressure sensor may be a sensor that measures a gas partial pressure in real time.

According to an example of the present invention, a partial oxygen pressure and pH may be measured in real time by using the microfluidic system simulating a lung tissue, and thus oxygen delivery into the system and pH inside the system may be adjusted (Experimental Example 3).

According to another aspect, the present invention provides a method for preparing a microfluidic system simulating a lung tissue, the method including: a step (1) of coating the porous membrane of the second layer with an extracellular matrix; a step (2) of seeding and culturing lung fibroblasts isolated from a human and vascular endothelial cells on the coated porous membrane; and a step (3) of seeding and culturing lung epithelial cells isolated from a human on an opposite side of the porous membrane on which the lung fibroblasts and the vascular endothelial cells are seeded. The microfluidic system simulating a lung tissue, the second layer, the porous membrane, the extracellular matrix, the lung epithelial cells, the lung fibroblasts, and the vascular endothelial cells are as described above.

According to an aspect of the present invention, the extracellular matrix of the step (1) may be one or more selected from the group consisting of laminin, collagen type I, collagen type II, collagen type III, collagen type IV, collagen type V, collagen type VI, integrin, entactin, fibronectin, elastin, proteoglycan, vitronectin, poly-D-lysine, polysaccharide, and gelatin, but is not limited thereto as long as it can attach the lung epithelial cells, the lung fibroblasts, or the vascular endothelial cells to the porous membrane.

According to an aspect of the present invention, the lung epithelial cells and the lung fibroblasts may be isolated from a human lung and may be specifically obtained by the isolating method as described below including: a step of dissociating a lung tissue sample isolated from a human; a step of adding microbeads that specifically bind to the lung epithelial cells and microbeads that specifically bind to the lung fibroblasts to the dissociated lung tissue sample; and a step of culturing the lung tissue sample bound with the added microbeads. In the isolating method, the microbeads that specifically bind to the lung epithelial cells may include a cluster of differentiation 326 (CD326), and the microbeads that specifically bind to the lung fibroblast may include anti-fibroblast microbeads. In this case, each of the lung epithelial cells and the lung fibroblasts may be isolated by types from the human lung tissue sample in which various kinds of cells mixed. The culturing of the lung tissue sample bound with the microbeads may be culturing at 4° C. to 37° C., specifically, may be culturing at 4° C. or higher, 5° C. or higher, 10° C. or higher, 15° C. or higher, 20° C. or higher, 25° C. or higher, 30° C. or higher, or 35° C. or higher, and may be culturing at 37° C. or below, 35° C. or below, 30° C. or below, 25° C. or below, 20° C. or below, 15° C. or below, 10° C. or below, 5° C. or below, or 4° C. or below, but the culturing temperatures of the lung epithelial cells and the lung fibroblasts may differ depending on types thereof, and are not limited to the above ranges. Further, if the gas and the medium-containing fluid is perfused in the microfluidic system simulating a lung tissue that includes the lung epithelial cells and the lung fibroblasts isolated from the human lung and the vascular endothelial cells, the cells are able to survive even when four, seven, or thirteen days elapsed (Experimental Example 1) unlike the single cell culture used in the related art, and thus a wide range of studies including a drug efficacy test for a lung disease treatment and other harmful substance tests may be conducted, and further, in-vitro diagnoses, personalized medicine prescription, and the like are possible.

According to an aspect of the present invention, the lung fibroblasts and the vascular endothelial cells in the step (3) may be mixed in the ratio of 1:1 to 25, and specifically, may be mixed in the ratio of 1:1 or more, 1:2 or more, 1:3 or more, 1:4 or more, 1:5 or more, 1:6 or more, 1:8 or more, 1:10 or more, 1:15 or more, or 1:20 or more, and may be mixed in the ratio of 1:25 or less, 1:20 or less, 1:15 or less, 1:10 or less, 1:8 or less, 1:6 or less, 1:5 or less, 1:4 or less, 1:3 or less, or 1:2 or less, but the ratio is not limited thereto.

According to another aspect, the present invention provides a microfluidic control method in a microfluidic system simulating a lung tissue, including: a microfluidic perfusion step of perfusing a gas into the first chamber of the microfluidic system simulating a lung tissue and perfusing the medium-containing fluid into the second chamber; and a step of measuring pH with a pH sensor of the system and measuring a gas partial pressure with the gas partial pressure sensor. The microfluidic system simulating a lung tissue, the first chamber, the second chamber, the gas, the medium-containing fluid, the pH measurement, and the gas partial pressure measurement are as described above.

According to an aspect of the present invention, the control method may further include a step of adjusting injection amount per hour of the gas and the medium-containing fluid to be injected to the microfluidic system simulating a lung tissue when the pH or the gas partial pressure measured in the step of measuring the pH and the gas partial pressure is different from pH or a gas partial pressure in a lung tissue of a human.

According to an aspect of the present invention, the gas partial pressure may be a partial oxygen pressure ($pO_2$).

Hereinafter, the configuration and effect of the present invention are described in more detail with reference to Examples and Experimental Examples. However, the following Examples and Experimental Examples are provided only for the purpose of illustration for better understanding of the present invention, and the scope and range of the present invention are not limited thereto.

[Example 1] Isolation of Lung Epithelial Cell and Lung Fibroblast from Human Lung Tissue In order to prepare a microfluidic system simulating a lung tissue in vivo, lung epithelial cells and lung fibroblasts are isolated from a human lung tissue by the following method.

[Example 1-1] Dissociation of Human Lung Tissue

Ten types of normal lung tissue samples (N-1 to N-10) of 0.39 to 1.37 g in Table 1 which are obtained from normal lung tissues among resected lung tissues of a lung cancer patient who underwent surgery, and two types of lung cancer tissue samples (C-1 and C-2) of 0.41 g in total in Table 1 which are obtained from cancer tissues among resected lung tissues of the lung cancer patient were stored for one or two days at 4° C. in a stock buffer (Miltenyi Biotec, Tissue Storage Solution), and then the tissue samples were divided by 0.4 to 0.5 g per C-tube.

TABLE 1

| Tissue Sample No. | Weight (g) |
| --- | --- |
| N-1 | 0.54 |
| N-2 | 0.52 |
| N-3 | 0.66 |
| N-4 | 0.70 |
| N-5 | 1.02 |
| N-6 | 1.17 |
| N-7 | 1.37 |
| N-8 | 0.64 |
| N-9 | 1.00 |
| N-10 | 0.39 |
| C-1 * | 0.28 |
| C-2 * | 0.13 |

* C-1 and C-2 which are lung cancer tissue samples were added to provide a total of 0.41 g of lung cancer tissue samples, and lung cancer cells in lung cancer tissues were isolated by the following method.

Then, 2.35 ml of a RPMI medium (Welgene, RPMI 1640), which is a serum-free medium, was dispensed to each of the C-tubes, enzymes of an enzyme kit (Miltenyi Biotec, Multi Tissue Dissociation Kit I) were added to each of the C-tubes according to the manual, washing was performed, moisture of the washed tissue samples was removed, and the tissue samples were transferred to each of the C-tubes. After that, scissors were put into each of the C-tubes to cut the tissues as finely as possible, the C-tubes were covered with lids and closed, each of the C-tubes was placed into a MACS (Magnetically Activated Cell Sorting) device (Miltenyi Biotec, GentleMACS™ Octo Dissociator) in order in a state of being placed in ice, and a program was executed. At this time, if an error occurred, the C-tube was taken out, mixing was performed, and the program was executed again. When the program was completed, the C-tubes were moved in a state of being placed in ice.

A filter was prepared in a 15-ml or 50-ml tube, the filter was soaked with about 2 ml of the serum-free RPMI medium, the lung tissue samples included in each of the C-tubes after the program completed were poured into the filter, and the C-tubes were further washed with 5 ml of the serum-free RPMI medium and poured into the filter. Thereafter, the supernatant was removed by centrifugation at 300×g for ten minutes, 1 ml of a red blood cell lysis buffer (Lonza, Red blood cell lysis buffer) was added, and the resultant was stood still for two minutes and re-suspended with 5 ml of the serum-free RPMI medium. Then, the supernatant was removed by centrifugation at 300×g for ten minutes, cells were counted after re-suspension with 5 to 10 ml of a cell medium (Lonza, EGM-2), the resultant was put into a T-175 flask with an endothelial cell medium (Lonza, EGM-2) or an epithelial cell medium (Lonza, SAGM) and cultured to dissociate lung tissues of a human. At this time, each C-tube was placed in one T-175 flask and cultured.

Figure 1:
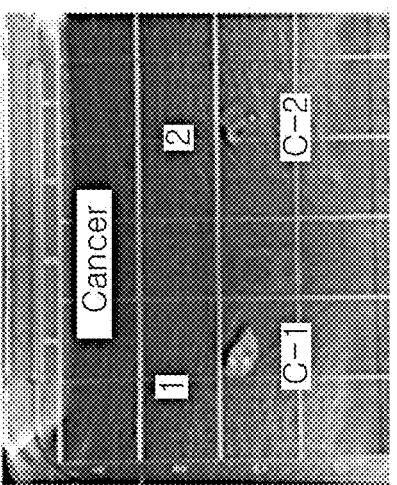
FIG. 1 is images of ten types of general lung tissue samples and two types of lung cancer tissue samples, which were used to prepare a microfluidic system simulating a lung tissue according to an example of the present invention.
Figure 1:
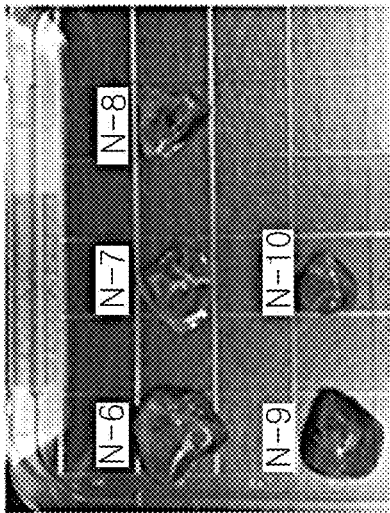
Figure 1:
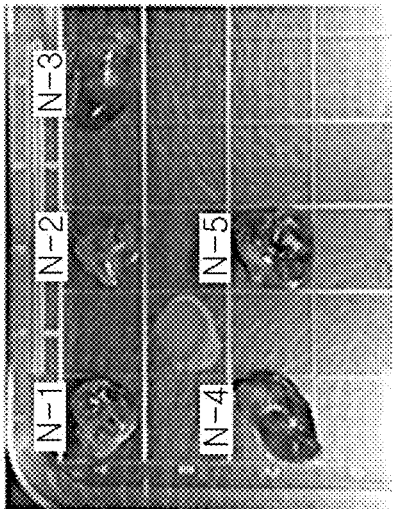
Figure 2A:
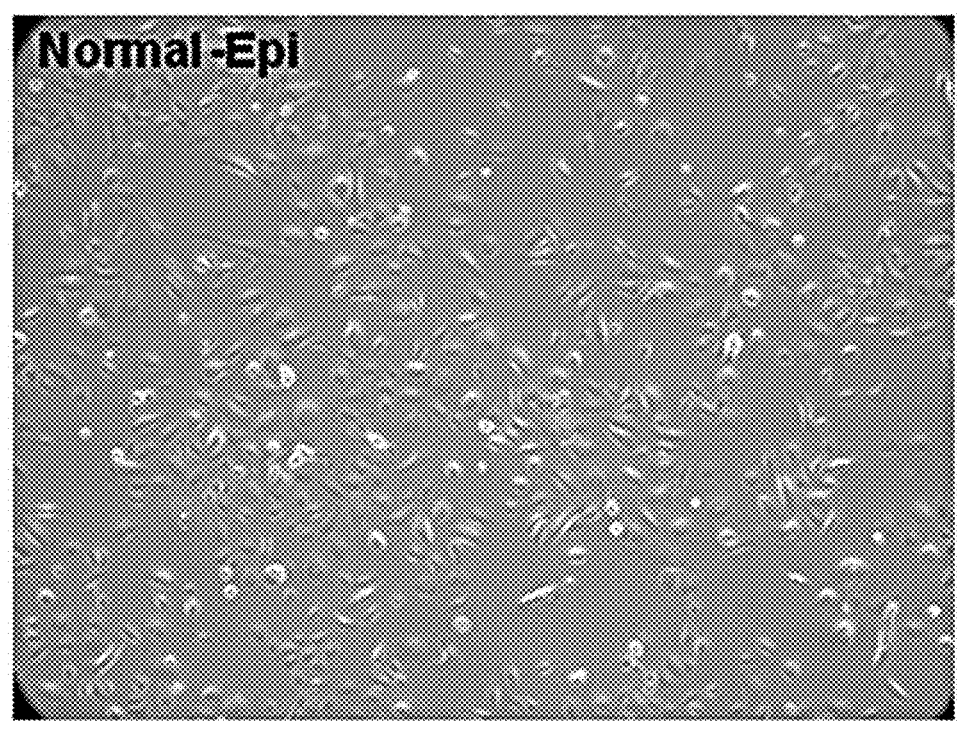
FIG. 2a is an image of lung epithelial cells (Normal-Epi) in a normal lung tissue dissociated by a method according to an example of the present invention.
Figure 2B:
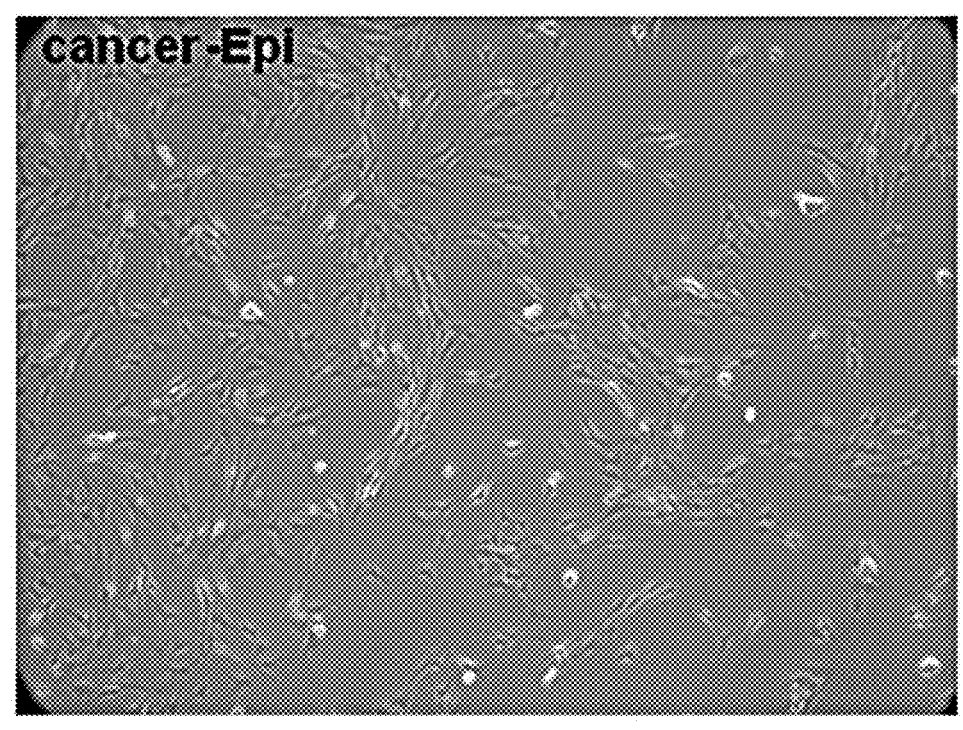
FIG. 2b is an image of lung cancer cells (cancer-Epi) in a lung cancer tissue dissociated by a method according to an example of the present invention.
Figure 3A:
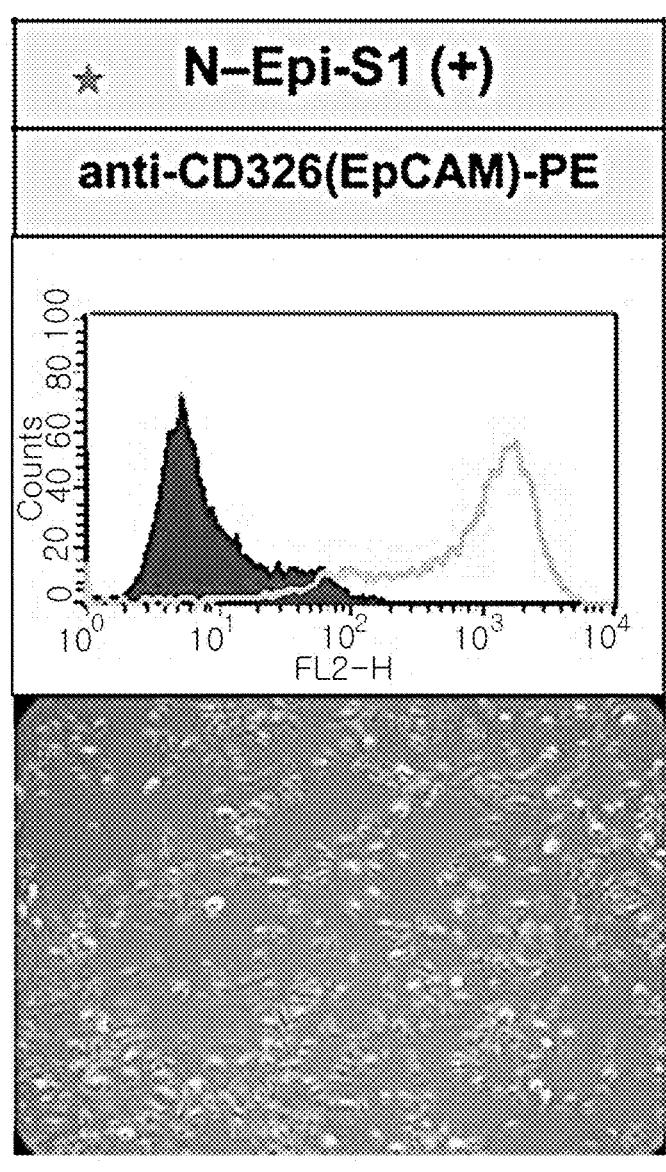
FIG. 3a is a view showing results of a FACS analysis of lung epithelial cells (N-Epi-S1) in a normal lung tissue isolated by a method according to an example of the present invention.
Figure 3B:
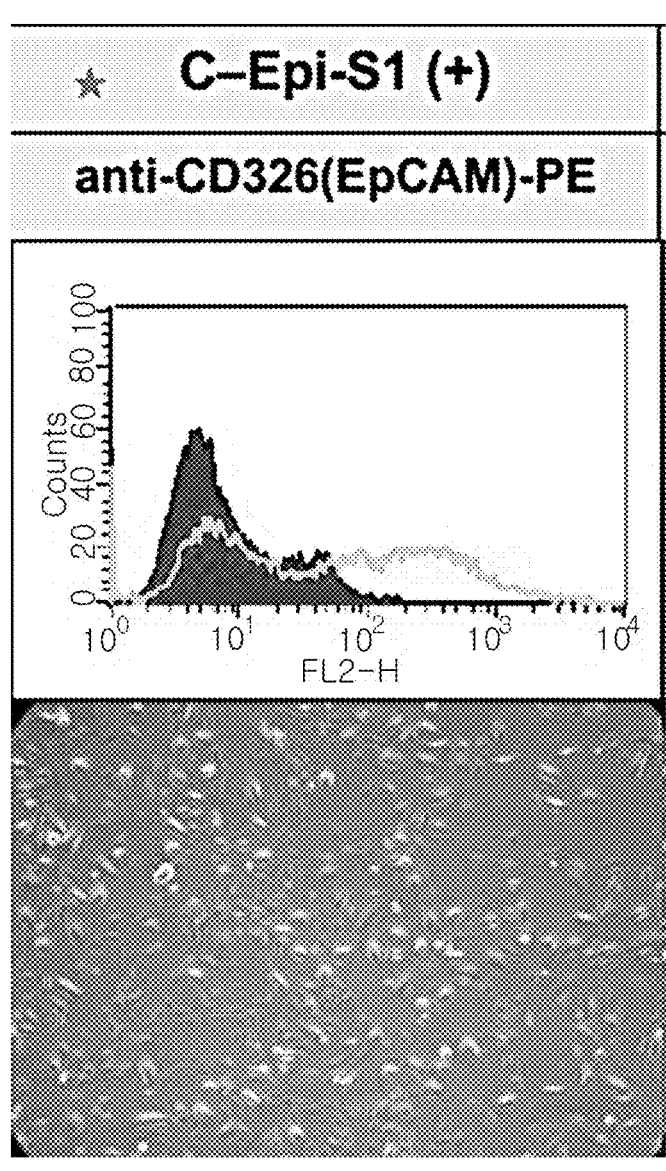
FIG. 3b is a view showing results of a FACS analysis of lung cancer cells (C-Epi-S1) in a lung cancer tissue isolated by a method according to an example of the present invention. In case of S1 obtained from a sample of a first patient, Epi-S1 was tested by using CD326-PE antibody, and the results show that cells were well isolated in all of the normal and cancer tissues.
Figure 4:
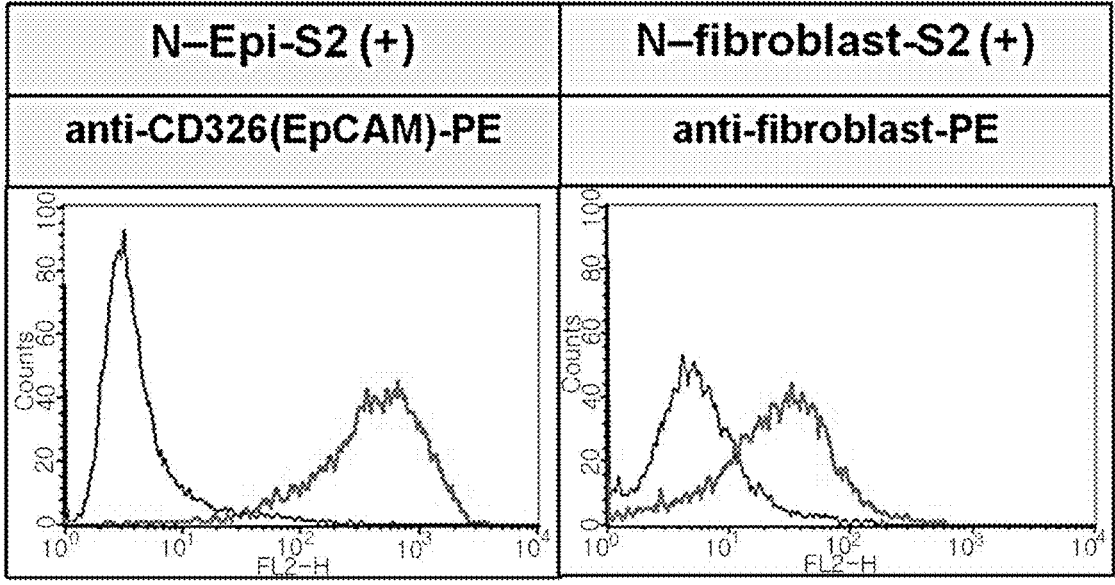
FIG. 4 is a view showing results of FACS analyses of lung epithelial cells (N-Epi-S2) and lung fibroblasts (N-fibroblast-S2) in a normal lung tissue isolated by a method according to an example of the present invention. S2 obtained from a sample of a second patient was also tested and confirmed as above.
Figure 5:
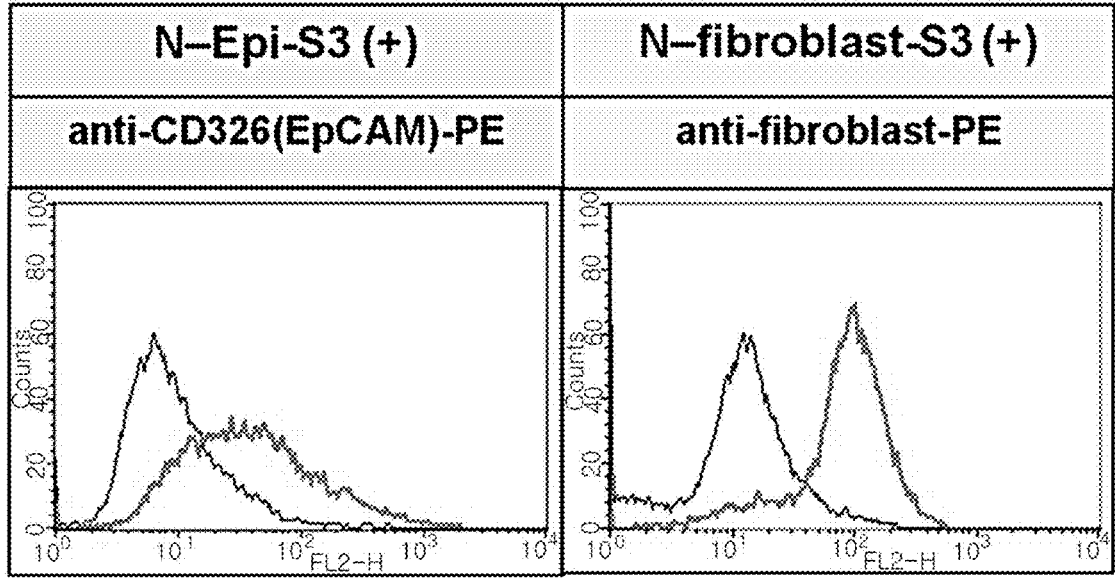
FIG. 5 is a view showing results of FACS analyses of lung epithelial cells (N-Epi-S3) and lung fibroblasts (N-fibroblast-S3) in a normal lung tissue isolated by a method according to an example of the present invention. S3 obtained from a sample of a third patient was also tested and confirmed as above.

The lung epithelial cells and lung fibroblasts (T-175 flasks in which the cells were cultured) in the dissociated lung tissues were observed with an optical microscope connected with a camera and images thereof were taken, and results thereof are as shown in FIG. 2a (the lung epithelial cells dissociated from the normal lung tissue sample (Normal-Epi)) and FIG. 2b (the lung cancer cells dissociated from the lung cancer tissue sample (cancer-Epi)).

[Example 1-2] Isolation of Lung Epithelial Cells and Lung Fibroblasts

The lung epithelial cells and the lung fibroblasts were isolated from the human lung tissues dissociated in Example 1-1 by the following process.

Specifically, the number of cells in the T-175 flask of Example 1-1 was counted to prepare about $5×10^6$ to $1×10^7$ of cells, and the cells were centrifuged at 300×g for ten minutes at room temperature to prepare three types of cell pellet suspensions, that is, a total of 300 ul of lung epithelial cell suspensions and a total of 80 ul of lung fibroblast suspensions. Here, the three types of suspensions were prepared by using a PEB buffer obtained by mixing the autoMACS rinsing solution (Miltenyi Biotec, #130-091-222) and the MACS BSA stock solution (Miltenyi Biotec, #130-091-376) in a volume ratio of 20:1, that is, by mixing 47.5 ml of the autoMACS rinsing solution and 2.5 ml of the MACS BSA stock solution.

Thereafter, in order to increase the purity of the isolated cells, 100 ul of the FcR blocking reagent (Miltenyi Biotec, #130-059-901) was added to the lung epithelial cell suspension, and the FcR blocking reagent was not added to the lung fibroblast suspension.

Thereafter, 100 ul of the CD326 microbeads (Miltenyi Biotec, #130-061-101) and 20 ul of the anti-fibroblast microbeads (Miltenyi Biotec, #130-050-601) were added to the lung epithelial cell suspension and the lung fibroblast suspension, respectively, and each was subjected to a vortex to be well mixed. The mixture of the CD326 microbeads and the lung epithelial cell suspension was cultured at 4° C. for 30 minutes, and the mixture of the anti-fibroblast microbeads and the lung fibroblast suspension were cultured at room temperature for 30 minutes. The culturing was performed in a refrigerator where the respective temperatures were maintained. After culturing, 1 ml of the PEB buffer was added to the mixture of the CD326 microbeads and the lung epithelial cell suspension and washed, and the each resultant was centrifugated at 300× g for 10 minutes. Also, 1 ml of PEB buffer was added to the mixture of the anti-fibroblast microbeads and the lung fibroblast suspension and washed, and the resultant was centrifugated at 300× g for three minutes. Then, 1 ml of the PEB buffer was added to each of the two types of mixtures to prepare two types of suspensions: a CD326 microbead-bound lung epithelial cell suspension and an anti-fibroblast microbead-bound lung fibroblast suspension.

In order to isolate (magnetic separation) the cells by using the magnetism of the microbeads in the suspension, an LS column was put on a magnetic body of a cell separator (Mitenyi Biotec, MidiMACS™ separator), and the column was washed with 3 ml of the PEB buffer. Then, after a 15-ml tube was placed under the column, a process of flowing the CD326 microbead-bound lung epithelial cell suspension into the column, collecting unlabeled negative cells in the 15-ml tube, and putting 3 ml of the PEB buffer into the column on ice was repeated three times for washing. In order to collect cells labeled with microbeads, the column was separated from the cell separator and put on a new 15-ml tube. Then, 5 ml of the PEB buffer was added to the column, a plunger was pushed until bubbles came out, and lung epithelial cells to which the CD326 microbeads are bound for labelling were collected in a 15-ml tube put under the column. The resultant was centrifugated at 300× g for ten minutes, the supernatant was removed, 10 ml of the cell medium was re-suspended, and the lung epithelial cells were counted. Labelled lung fibroblasts were respectively collected from the anti-fibroblast microbead-bound lung fibroblast suspension by the cell isolation method using the microbead magnetism, and respective cells were centrifugated, re-suspended, and counted by the same method.

[Example 1-3] Confirmation of Isolation of Lung Epithelial Cells and Lung Fibroblasts by FACS Analysis In order to confirm whether the lung epithelial cells and the lung fibroblasts isolated in Example 1-2 were isolated by types, a fluorescence activated cell sorter (FACS) analysis was performed.

Figure 6:
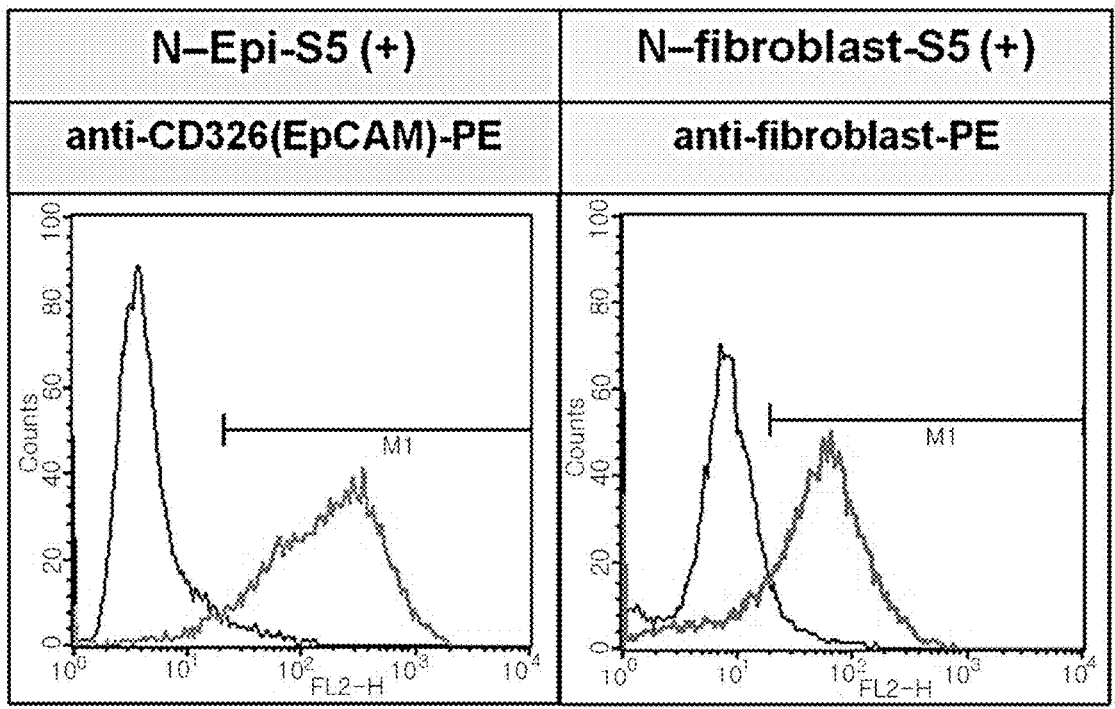
FIG. 6 is a view showing the results of FACS analyses of lung epithelial cells (N-Epi-S5) and lung fibroblasts (N-fibroblast-S5) in a normal lung tissue isolated by a method according to an example of the present invention.

Specifically, a PEB buffer obtained by mixing the autoMACS rinsing solution (Miltenyi Biotec, #130-091-222) and the MACS BSA stock solution (Miltenyi Biotec, #130-091-376) in a volume ratio of 20:1, that is, by mixing 47.5 ml of the autoMACS rinsing solution and 2.5 ml of the MACS BSA stock solution was prepared, the lung epithelial cells and the lung fibroblasts isolated in Example 1-2 with trysin/EDTA (Welgene, LS015-01) were denoted by S1 (first) and S2 (second) according to the order of obtaining the patient samples, normal cells were denoted by N, and cancer cells were denoted by C. N1 to C2 are numbers by classifying two types of tissues which were cut in the unit of 0.5 g. The two types of cells were respectively counted to obtain $2 \times 10^5$ of cells each and centrifugated at 300× g for ten minutes. The FACS analysis results are shown in FIG. 6.

As shown in FIGS. 3 to 6, in the FACS histogram results, black lines indicate control groups with no antibodies attached, and lines in colors other than black indicate amounts of cells in the experimental groups to which the antibody is attached. By confirming that the lines of the experimental groups are much different from the black line of the control groups, it can be confirmed that the isolation was successful.

[Example 1-4] Confirmation of Isolation of Lung Epithelial Cells and Lung Fibroblasts by Immuno Fluorescence Assay In order to confirm whether the lung epithelial cells and the lung fibroblasts isolated in Example 1-2 are isolated by types, the immuno fluorescence assay was performed.

Figure 7A:
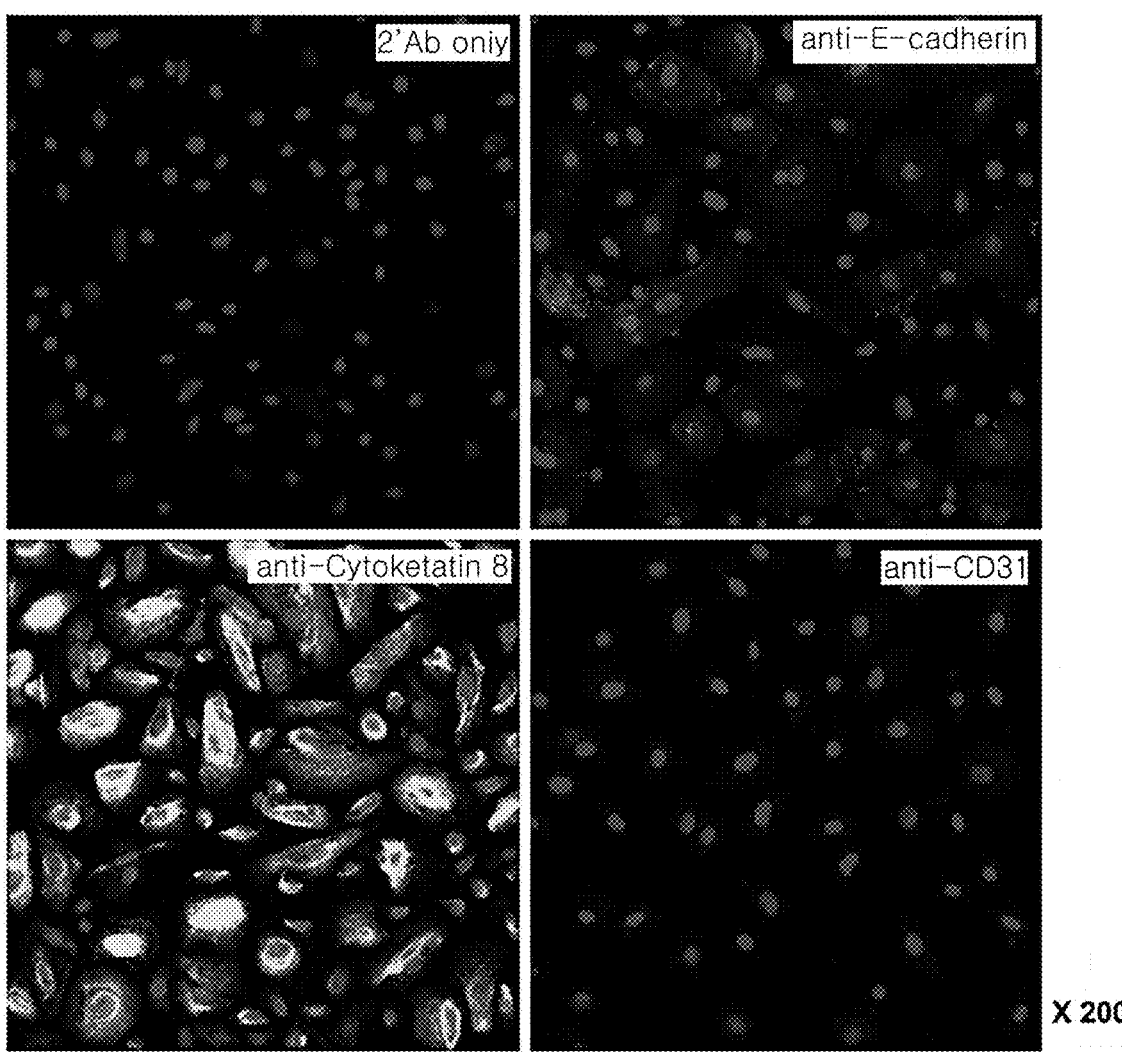
FIGS. 7a and 7b are views showing results of immunofluorescence analyses of the lung epithelial cells (N-epi-S1 and N-epi-S2) in a normal lung tissue isolated by a method according to an example of the present invention.

(1) Confirmation of Isolation of Lung Epithelial Cells by Immuno Fluorescence Assay First, after three days since the lung epithelial cells were isolated in Example 1-2, N-epi-S1 was reacted, as a primary antibody, with mouse monoclonal antibody anti-E Cadherin (mouse mAb anti-E Cadherin) (Santa Cruz, sc-8426) that is an epithelial cell marker in the ratio of 1:100 and with mouse monoclonal antibody anti-cytokeratin 8 (mouse mAb anti-cytokeratin 8) (Santa Cruz, sc-73480) that is another epithelial cell marker in the ratio of 1:100, and was reacted, as a secondary antibody, with goat anti-mouse IgG-Alexa 488 (Goat anti-mouse IgG-Alexa 488) (MP, A111001) in the ratio of 1:100, then the resultants were photographed with a confocal microscope (Carl Zeiss, LSM710), and the results are illustrated in FIG. 7a. In addition, the immuno fluorescence assay was also performed with N-epi-S2, which was the lung epithelial cells isolated in Example 1-2, except that it was reacted, as a primary antibody, with mouse monoclonal antibody anti-E Cadherin (Abcam, ab1416) in the ratio of 1:50 instead of mouse monoclonal antibody anti-E Cadherin (Santa Cruz, sc-8426) that is an epithelial cell marker, and was reacted, as a secondary antibody, with donkey anti-mouse IgG-Alexa 488 (Abcam, ab150105) in the ratio of 1:100 instead of goat anti-mouse IgG-Alexa 488 (MP, A111001), and that the resultants were photographed with a confocal microscope at a magnification of ×200. The results of N-epi-S2 are illustrated in FIG. 7b.

Figure 7B:
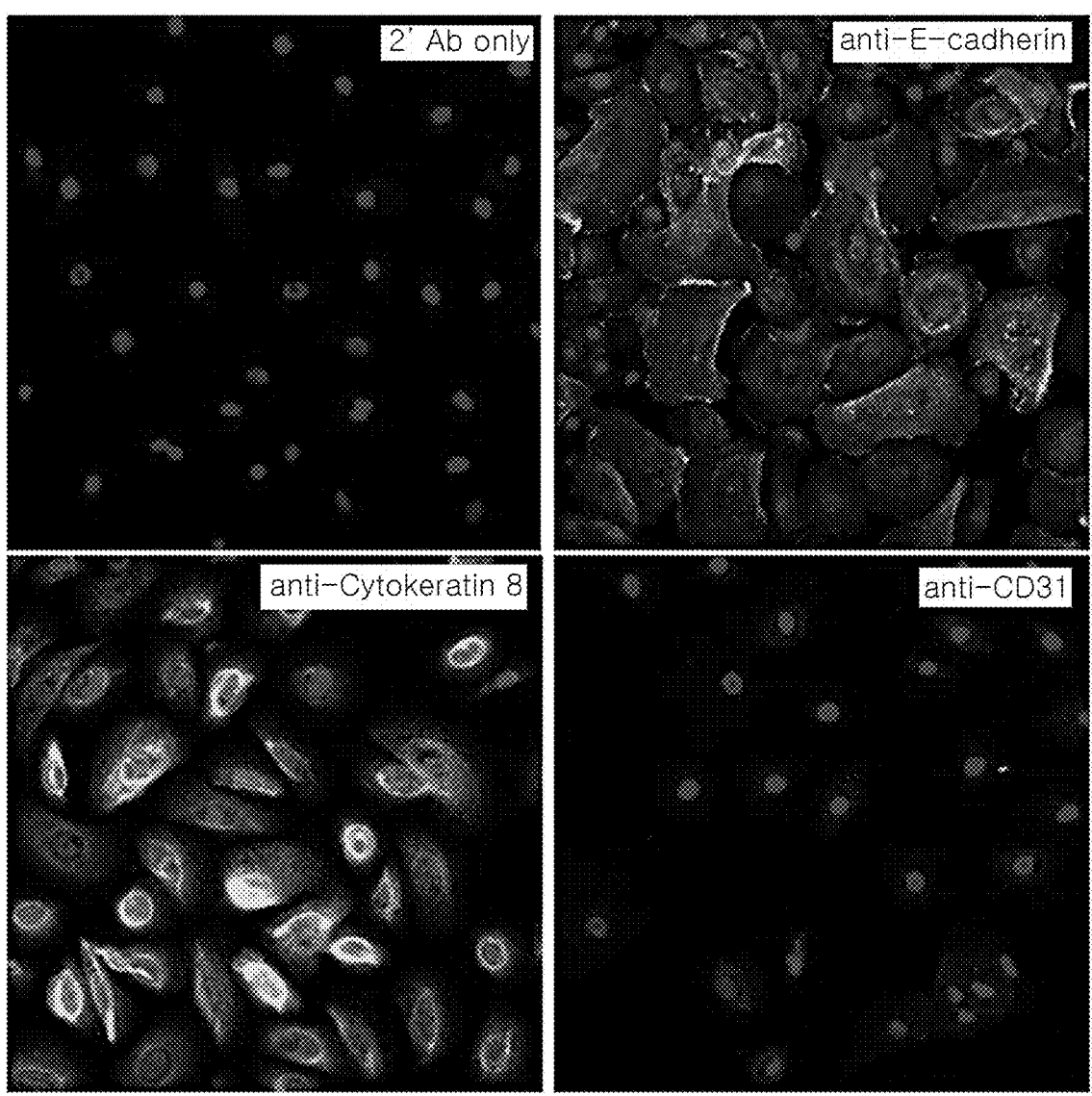
Figure 7C:
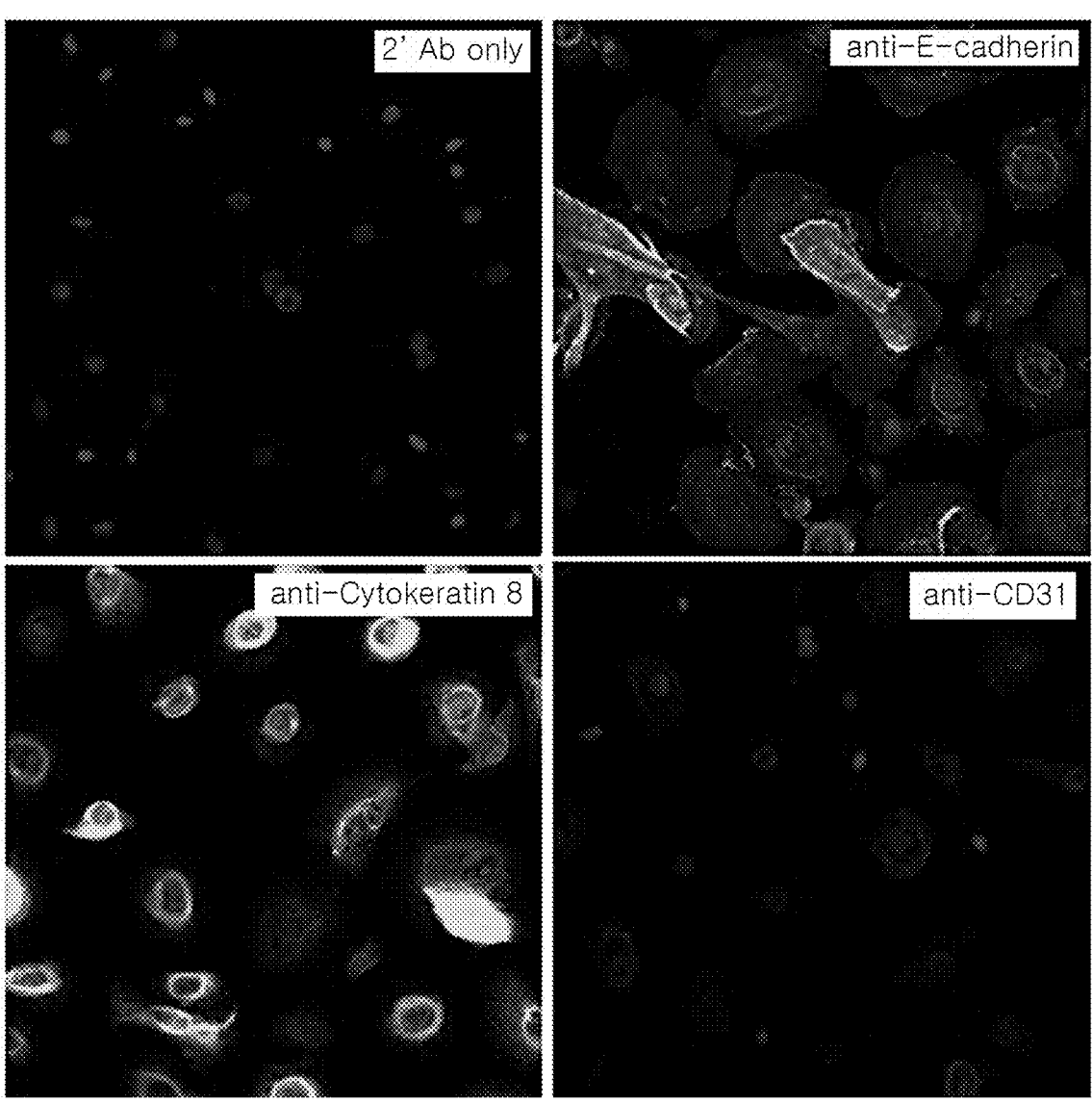
FIG. 7c is a view showing results of immunofluorescence analyses of commercially available small airway epithelial cells (SAEC) as a control.

Meanwhile, the immuno fluorescence assay was performed with small airway epithelial cells (SAEC) (Lonza, CC-2547) as a control group in the same method as the immuno fluorescence assay method of N-epi-S2, and the result of the control group is illustrated in FIG. 7c.

As illustrated in FIGS. 7a and 7b, it was confirmed that the lung epithelial cells isolated from actual human in Example 1-2 expressed E-Cadherin and cytokeratin 8 in the same manner as the commercially available epithelial cells of the control group (FIG. 7c) expressed E-Cadherin and cytokeratin 8.

(2) Confirmation of Isolation of Lung Fibroblasts by Immuno Fluorescence Assay

Figure 8:
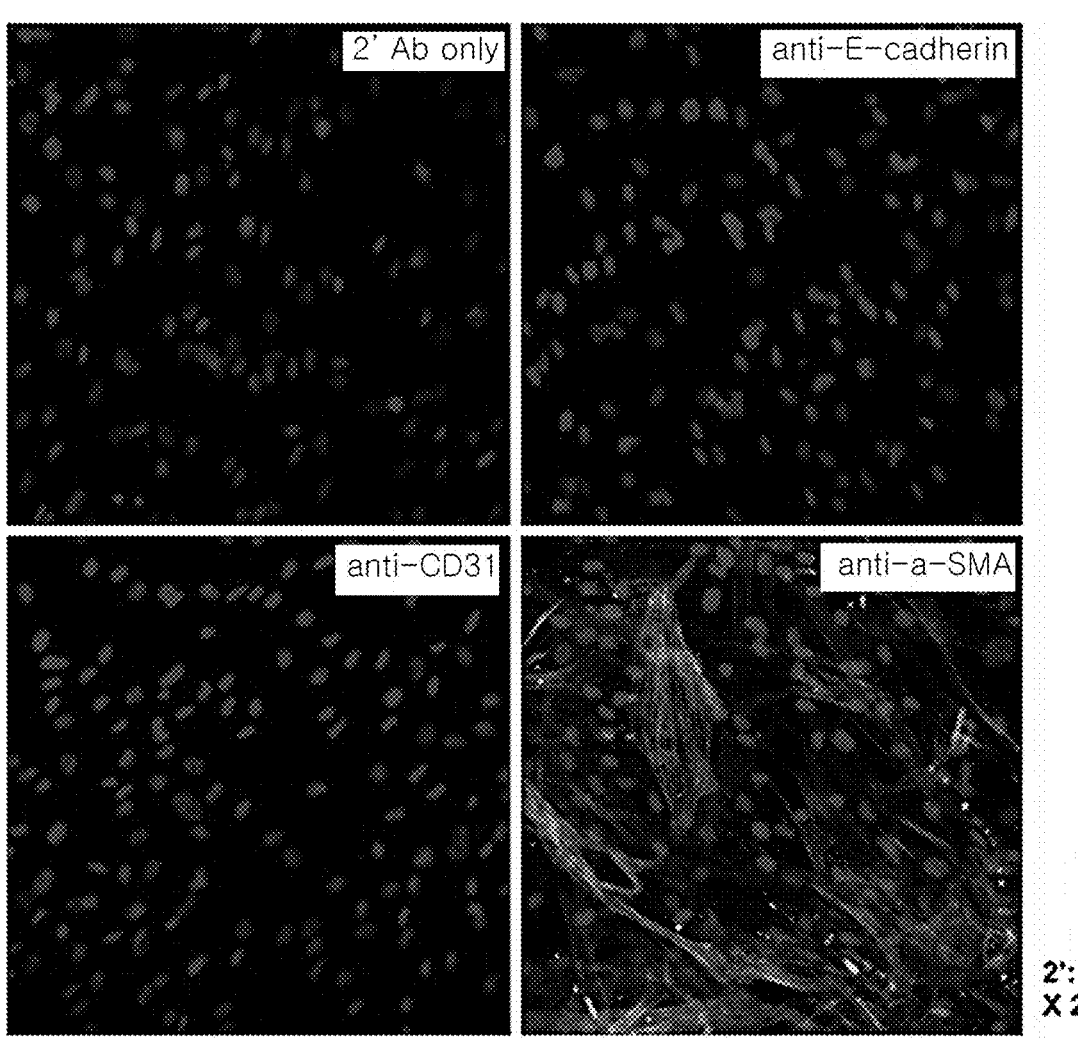
FIG. 8 is a view showing results of immunofluorescence analyses of lung fibroblasts (N-Fibroblast-S3) in a normal lung tissue isolated by a method according to an example of the present invention.

First, after three days since the lung fibroblasts were isolated in Example 1-2, N-Fibroblast-S3 was reacted, as a primary antibody, with mouse monoclonal antibody anti-E Cadherin (mouse mAb anti-E Cadherin) (Santa Cruz, sc-8426) that is an epithelial cell marker in the ratio of 1:100, mouse monoclonal antibody anti-CD31 (mouse mAb anti-CD31) (Santa Cruz, sc-65260) that is an endothelial cell marker in the ratio of 1:100, and mouse monoclonal antibody anti-α smooth muscle actin (mouse mAb anti-α smooth muscle actin) (Abcam, ab7817) that is a fibroblast marker in the ratio of 1:200, and reacted, as a secondary antibody, with goat anti-mouse IgG-Alexa 488 (Goat anti-mouse IgG-Alexa 488) (MP, A111001) in the ratio of 1:100, then the resultants were photographed with a confocal microscope (Carl Zeiss, LSM710), and the results are illustrated in FIG. 8.

As illustrated in FIG. 8, it was confirmed that the lung fibroblasts isolated from actual human in Example 1-2 only express the a smooth muscle actin.

From the results of Examples 1-3 and 1-4, it is confirmed that the lung epithelial cells and the lung fibroblasts can be respectively isolated from actual human by the processes of Examples 1-1 and 1-2.

[Example 2] Preparing of Microfluidic System Simulating Lung Tissue Including Lung Epithelial Cell and Lung Fibroblasts Isolated from Human Lung Tissues and Commercially Available Vascular Endothelial Cells By using the lung epithelial cell and lung fibroblasts isolated from the human lung tissue obtained in Example 1and the commercially available vascular endothelial cells, the microfluidic system for simulating the lung tissue in vivo was prepared by the following method. Further, in addition to the lung epithelial cells obtained in Example 1, Calu-3 (ATCC) can be additionally used.

First, the porous membrane of the middle layer of the Organ-on-a-Chip Platform (Micronit, the Netherlands) (when the pore size is 0.45 μm, the pore density is $2.00^6$ $cm^2$, and when the pore size is 3 μm, the pore density is $8.00^5$ $cm^2$) was coated with a mixture of 0.001% fibronectin (Sigma, F0895, 5 mg), 0.03 mg/ml collagen (Sigma, Collagen Type I solution, 1 VL content), and 0.001 mg/ml bovine serum albumin (BSA) (Miltenyi Biotec, MACS BSA stock #130-091-376, 75 ml) at 4° C. for one night and dried. Thereafter, $2\times10^5/100$ μl of the lung epithelial cells (N-Epi-S2 (p3: subculture three times) or Calu-3) isolated from human obtained in Example 1 were seeded for two hours on the lower surface of the porous membrane and then cultured at 37° C. for one hour (FIG. 9a). Thereafter, a mixture of $2\times10^5/50$ μl of the commercially available vascular endothelial cells (HUVEC(p2), LONZA) and $0.4\times10^5/50$ μl of the lung fibroblasts (N-Fibroblast-S5 (p8)) isolated from human obtained in Example 1 was seeded on the opposite side of the surface of the porous membrane where the lung epithelial cells were seeded and cultured at 37° C. for four days (FIG. 9b). FIG. 9c is a view schematically illustrating a state in which the lung epithelial cells, the vascular endothelial cells, and the lung fibroblasts were attached to the porous membrane.

In accordance with the manual of the Organ-on-a-Chip Platform, the microfluidic system simulating a lung tissue was prepared to include the middle layer including the lung epithelial cells, the vascular endothelial cells, and the lung fibroblasts. FIG. 10a is a view schematically illustrating the microfluidic system simulating a lung tissue, and FIG. 10b is a view schematically illustrating the porous membrane of the middle layer including three types of cells in the said system.

In addition, a $pO_2$ sensor (Presens, Microox4) was attached to the surface of the first layer (or the upper layer) facing the first chamber (gas perfusion chamber) of the system as a gas partial pressure sensor, and a pH sensor (Presens, pH-1 mini V2) was attached to the surface of the third layer (or a lower layer) facing the second chamber (chamber for perfusing the medium-containing fluid). FIG. 11 is a view schematically illustrating the microfluidic system simulating a lung tissue to which the sensor is attached.

[Example 3] Fluid Perfusion to Microfluidic System Simulating Lung Tissue

As the air coming out by connecting an air pump, an air sensor, and a tubing, the gas consisting of actual atmospheric air in room temperature was injected into the first inlet of the first layer (or the upper layer) of the microfluidic system simulating a lung tissue manufactured in Example 2, the medium (STEMCELL, PneumaCult™-ALI #05001, 500 ml) was injected into the second inlet, and the resultant was perfused for four days at the speed of 5 μl/min to prepare the microfluidic system similar to the lung tissue in vivo. The pressure range of the perfused gas was adjusted at a cycle of 10 to 12 times per minute through a program to simulate the respiration movement (FIGS. 14e and 14f).

[Experimental Example 1] Confirmation of Viability of Cells in Microfluidic System Simulating Lung Tissue Whether the lung epithelial cells, the lung fibroblasts, and the vascular endothelial cells survived in the system after several days were elapsed since the fluid was perfused as in Example 3 in the microfluidic system simulating a lung tissue manufactured in Example 2 was confirmed. An experiment for confirmation of viability after the cells were cultured was confirmed by respectively staining live and dead cells at 37° C. for 30 minutes by using LIVE/DEAD™ Viability/Cytotoxicity kit (Invitrogen, #L3224) and using a confocal microscope (Carl Zeiss, LSM710).

FIGS. 12a to 12d show results of the immunofluorescence analysis when four days elapsed after the fluid perfusion, and it is confirmed that the lung epithelial cells, the lung fibroblasts, and the vascular endothelial cells were survived in the microfluidic system simulating a lung tissue even after four days elapsed.

In addition, FIGS. 13a and 13b show results of the immunofluorescence analysis when two days elapsed after the fluid perfusion, and FIGS. 14a and 14b show results of the immunofluorescence analysis when four days elapsed after the fluid perfusion. The results confirmed that the lung epithelial cells, the lung fibroblasts, and the vascular endothelial cells were survived in the microfluidic system simulating a lung tissue after two and four days elapsed.

For reference, in the above, FIGS. 12a to 12d and FIGS. 13a and 13b show a case of using lung epithelial cells obtained in Example 1, and FIGS. 14A and 14B show a case of using Calu-3.

[Experimental Example 2] Confirmation of Oxygen Delivery and pH Adjustment in Microfluidic System Simulating Lung Tissue In order to confirm the oxygen delivery and the pH adjustment which are important and unique characteristics of the lung, the fluid was perfused as in Example 3 in the microfluidic system simulating a lung tissue prepared in Example 2, and the partial oxygen pressure and the pH were measured. The process of the pH sensor measurement is as follows. A pH sensor was attached to the inside between upper and lower glass chips and was brought into contact from the outside with an optic fiber cable line of a sensor pH-1 mini V2 transmitter connected to a computer for monitoring while the cells were cultured, and pH was measured in real time. The $O_2$ sensor measurement process is as follows. The $O_2$ sensor was attached to the inside between upper and lower glass chips and was brought into contact from the outside with an optical fiber cable line of a $pO_2$ Microox4 transmitter while the cells were cultured, and $pO_2$ was measured in real time.

FIGS. 15a and 15b are diagrams illustrating results obtained by perfusing the fluid in the microfluidic system simulating a lung tissue according to an example of the present invention and then measuring pH (FIG. 15a) and $pO_2$ (FIG. 15b) by using the pH sensor and the $pO_2$ sensor inside thereof.

As illustrated in FIGS. 15a and 15b, it was confirmed that the partial oxygen pressure inside the system was 20% which corresponds to the atmospheric partial oxygen pressure, and it was confirmed that the pH was 7.0 to 8.0 that was pH of the injected cell medium.

That is, it was understood that, when using the microfluidic system simulating a lung tissue prepared in Example 2, a partial oxygen pressure and pH can be measured in real time, and thus it is able to adjust the delivery of oxygen into the system and pH inside the system.

INDUSTRIAL APPLICABILITY

The microfluidic system simulating a lung tissue according to an aspect of the present invention enables a wide range of studies including implementation of lung disease models, a test for therapeutic drug efficacy, and other harmful substance tests, and is further applicable to in-vitro diagnosis and personalized medicine prescription.

The invention claimed is:

1. A microfluidic control method in a microfluidic system simulating a lung tissue, the system comprising:
   a first layer; a second layer; a third layer;
   a first chamber for gas perfusion between the first layer and the second layer; and a second chamber for medium-containing fluid perfusion between the second layer and the third layer,
   wherein the second layer includes a porous membrane,
   the porous membrane includes lung epithelial cells, lung fibroblasts, and vascular endothelial cells,
   the lung epithelial cells face the first chamber,
   the vascular endothelial cells face the second chamber;
   the method comprising
   a microfluidic perfusion step of perfusing gas to the first chamber of the microfluidic system and perfusing the medium-containing fluid to the second chamber,
   wherein the porous membrane includes the lung epithelial cells that are seeded and cultured on one side of the porous membrane, and the porous membrane includes the lung fibroblasts and the vascular endothelial cells that are seeded and cultured on the opposite side of the porous membrane,
   wherein the lung epithelial cells are alveoli epithelial cells, and
   wherein the first layer comprises one or more gas partial pressure sensors and the third layer comprises one or more pH sensors;
   a step of adjusting a pressure of a perfusion gas for simulating respiration movement; and
   a step of measuring pH by the pH sensor of the system and measuring a gas partial pressure by the gas partial pressure sensor.

2. The microfluidic control method in the microfluidic system simulating a lung tissue according to claim 1,
   wherein when the pH or the gas partial pressure measured in the step of measuring pH and gas partial pressure is different from pH or a gas partial pressure in a human lung tissue, the control method further comprises a step of adjusting an injection amount per hour of the gas and the medium-containing fluid injected into the microfluidic system simulating a lung tissue.

3. The microfluidic control method in the microfluidic system simulating a lung tissue according to claim 1,
   wherein the gas partial pressure is a partial oxygen pressure ($pO_2$).

* * * * *